United States Patent [19]
Noding et al.

[11] Patent Number: 5,425,869
[45] Date of Patent: Jun. 20, 1995

[54] POLYMERIC FILM-BASED ELECTROCHEMICAL SENSOR APPARATUS

[75] Inventors: Stephen A. Noding, Brusly; Charles B. Miller, Denham Springs; Duane K. Wolcott; Carolyn Ribes, both of Baton Rouge; all of La.; Sten A. Wallin, Midland, Mich.; Beatriz Cisneros, Baton Rouge, La.

[73] Assignee: The Dow Chemical Company, Midland, Mich.

[21] Appl. No.: 232,783

[22] Filed: Apr. 20, 1994

Related U.S. Application Data

[63] Continuation-in-part of Ser. No. 34,989, Mar. 23, 1993, abandoned, which is a continuation-in-part of Ser. No. 872,259, Apr. 22, 1992, abandoned.

[51] Int. Cl.$^6$ .............................. G01N 27/26
[52] U.S. Cl. ..................... 204/418; 204/416; 204/421; 204/431; 204/432
[58] Field of Search ............... 204/415, 416, 418, 419, 204/421, 426, 428, 413, 431, 432

[56] References Cited

U.S. PATENT DOCUMENTS 4,948,490 8/1990 VenKatasetty ...................... 204/415

OTHER PUBLICATIONS

EG&G Princeton Applied Research; Interdigitated Microsensor Electrodes No month and year available.
N. F. Sheppard, Jr; R. C. Tucker; C. Wu, Electrical Conductivity Measurements Using Microfabricated Interdigitated Electrodes 1993 1199–1202, Anal. Chem. No month available.
W. H. Christensen; D. N. Sinha; S. F. Agnew, Conductivity of polystyrene film upon exposure to nitrogen dioxide: a novel $NO_2$ sensor 1993 149–153, Sensors and Actuators No month available.

Primary Examiner—John Niebling
Assistant Examiner—Bruce F. Bell

[57] ABSTRACT

An apparatus for detecting a given compound or changes in the concentration of such compound from a baseline concentration by means of a solid phase, film electrolyte, and being operable in a dissociative, galvanic or amperometric mode.

19 Claims, 20 Drawing Sheets

POLYMERIC FILM-BASED ELECTROCHEMICAL SENSOR APPARATUS

This application is a continuation-in-part of U.S. patent application Ser. No. 08/034,989, filed Mar. 23, 1993 now abandoned, as a continuation-in-part of U.S. patent application Ser. No. 07/872,259 filed Apr. 22, 1992, now abandoned.

This invention relates generally to electrochemical apparatus and detection methods.

Electrochemical detectors or sensors have been known for many years. One early sensor has electrodes forming a part of the electrochemical cell or couple and which are separated by means of a porous layer. The porous layer permits a restricted flow of liquid electrolyte, thereby completing the electrochemical circuit between the electrodes in the sensor. Although the upscale response of this sensor is excellent, large reservoirs of liquid electrolyte are typically required to be maintained. In addition, the porous layer permits a substantial diffusion of sample and of all the constituents thereof throughout the electrolyte. The result is the possibility of contamination or poisoning of the electrodes, and of direct interference in the quantitative measurement by substances present in the sample other than those being determined.

A second sensor utilizes a static liquid electrolyte and a permeable barrier to retain the electrolyte. Less electrolyte is for this reason required, but in the event of relatively large concentrations being encountered of the substance to be determined, the electrolyte again can be infused with that substance. The permeable barrier, however, hinders the quick recovery of the sensor after this infusion.

Another type of prior art electrochemical detector which has found wide acceptance and good success in the chemical process industry uses a static liquid electrolyte and an ion-exchange membrane to prevent the electrolyte from being contaminated with the substance to be detected. One such liquid electrolyte electrochemical sensor is described in U.S. Pat. No. 4,333,810 to Wolcott, issued Jun. 8, 1982.

However, liquid electrolyte electrochemical sensors even as described in the '810 patent have still required frequent maintenance checks. There is also a susceptibility to leaks if the detectors become inverted or require mounting in an inverted position, or if the detectors are needed in non-ambient pressure or vacuum situations or environments, or in high temperature environments.

A different type of electrochemical sensor is described in U.S. Pat. No. 4,948,490 to Venkatasetty, wherein a solid electrolyte film is used in an environmental sensor. The film includes a tetraalkylammonium salt with a complexing polymeric matrix material, and is prepared from a solution of salt and polymer in one or more aprotic solvents. A plasticizer can be included in the solution and evaporated with the solvent(s) in film formation.

U.S. Pat. No. 4,925,544 to Goldring describes hybrid film-based electrochemical sensors, wherein a "selectively permeable membrane" (which may be a Teflon TM film) separates the analyte and an electrically conductive film comprised of a homogeneous dispersion of a polymeric matrix phase, a high dielectric constant plasticizer which remains in the film and an electrically conductive salt dissolved in the continuous plasticizer phase. This dispersion is recited as being substantially free of water. A transcutaneous oxygen sensor is specifically exemplified which utilizes a plasticized film of poly(vinylidene fluoride), a propylene carbonate plasticizer, and tetraethylammonium perchlorate and tetraethyammonium chloride salts.

The present invention provides in overview a novel and inventive apparatus for detecting a compound of interest (which will usually, but not necessarily, be in the gas phase) through the formation of ionic species therefrom, compounds of likely interest including for example, hydrochloric acid, nitric acid, acetic acid, hydrofluoric acid, chlorine, bromine, nitrogen oxides (e.g., nitrogen dioxide), sulfuryl fluoride, ozone, oxygen, sulfur trioxide, sulfur dioxide, hydrogen sulfide, ammonia, carbon dioxide, alkyl chlorides (e.g., methyl chloride), alkyl bromides (e.g. methyl bromide), unsaturated hydrocarbons (e.g. benzene, ethylene, propylene, butylene, toluene and the like), water, phosgene, carbon monoxide, and hydrogen among many others. The present apparatus enables the detection of specific compounds in ambient atmospheres, but more importantly (and unlike the earlier solid electrolyte film-based sensors taught by Goldring and Venkatasetty) enables the real-time detection of such compounds under harsh industrial process conditions.

In a first embodiment, the inventive apparatus includes in an electrical circuit: a non-plasticized polymer film which acts in an electrolytic capacity and which is comprised of i) a substantially inert, noncomplexing polymeric matrix, ii) a complexing agent and iii) an electrolyte material dissociatingly soluble in the complexing agent, all of which are compatible with one another and with ionic species generated from a compound of interest; electrodes in electrical contact with the polymer film; and measuring apparatus associated with said electrodes for measuring a change in voltage or current in the circuit responsive to the presence of the compound in the film's environment or responsive to a change in the concentration of such compound in such environment from a baseline concentration.

In a second embodiment, the inventive apparatus includes: a polymer film which acts in an electrolytic capacity but which does not have the electrolyte material incorporated therein that is included in the first embodiment, and which is otherwise comprised of i) a substantially inert, noncomplexing polymeric matrix and ii) a complexing agent which is compatible with ionic species generated from a compound of interest, the complexing agent being either of a plasticizing or nonplasticizing nature with respect to said noncomplexing polymeric matrix; electrodes in electrical contact with the polymer film; and measuring apparatus associated with said electrodes for measuring a change in voltage or current in the circuit responsive to the presence of the compound in the film's environment or responsive to a change in the concentration of such compound in such environment from a baseline concentration.

Various apparatus are thus contemplated which employ an ion-conductive polymeric film for carrying out any of a number of conventionally known electrochemical sensing techniques, for example, coulometry, chronopotentiometry, AC (alternating current) voltammetry, pulsing and scanning potential techniques, amperometry, conductimetry, etc.

In one more particular version, operable in what shall be referred to as the dissociative mode, the apparatus includes in an electrical circuit: a polymer film of the type described above in conjunction with the second embodiment, wherein the complexing agent dissociates an ionizable compound of interest into ionic species and is compatible with such ionic species; working and counter electrodes in electrical contact with the polymer film; a power source for applying a voltage between the working and counter electrodes; and measuring apparatus associated with the electrodes and which indicates a change in voltage or current in the circuit responsive to the ionizable compound contacting the polymer film and being dissociated therein into ionic species or responsive to a change in the number of molecules of such ionizable compound contacting the polymer film over a period of time from a baseline number.

In another version, operable in what shall be referred to as the galvanic mode, a polymer film is used of a type described in conjunction with the first embodiment above as including an electrolyte material, and the working and counter electrodes are composed of sufficiently dissimilar materials so as to provide a net spontaneous oxidation or reduction of a compound of interest to ionic species and a corresponding response which is measured by associated measuring apparatus.

A still further version, operable in an amperometric mode, utilizes an electrical power source to apply a potential between a working electrode and a counter electrode in a two-electrode arrangement or between a working electrode and a reference electrode in a three-electrode arrangement, thereby inducing an oxidation or reduction of a compound of interest and a corresponding response which is measured by the measuring apparatus.

In other, more particular aspects still of the present invention, the electrodes of these various apparatus are in the form of interdigitated microsensor electrode arrays (IMEs), and several such apparatus are employed in an array for detecting a plurality of species in a given environment (through association with or use of a microprocessor or like data processing means).

BRIEF DESCRIPTION OF THE DRAWINGS

The present invention can be more easily understood by reference to the following drawings, which are not to scale and which have like numbers referring to like parts.

Figure 1:
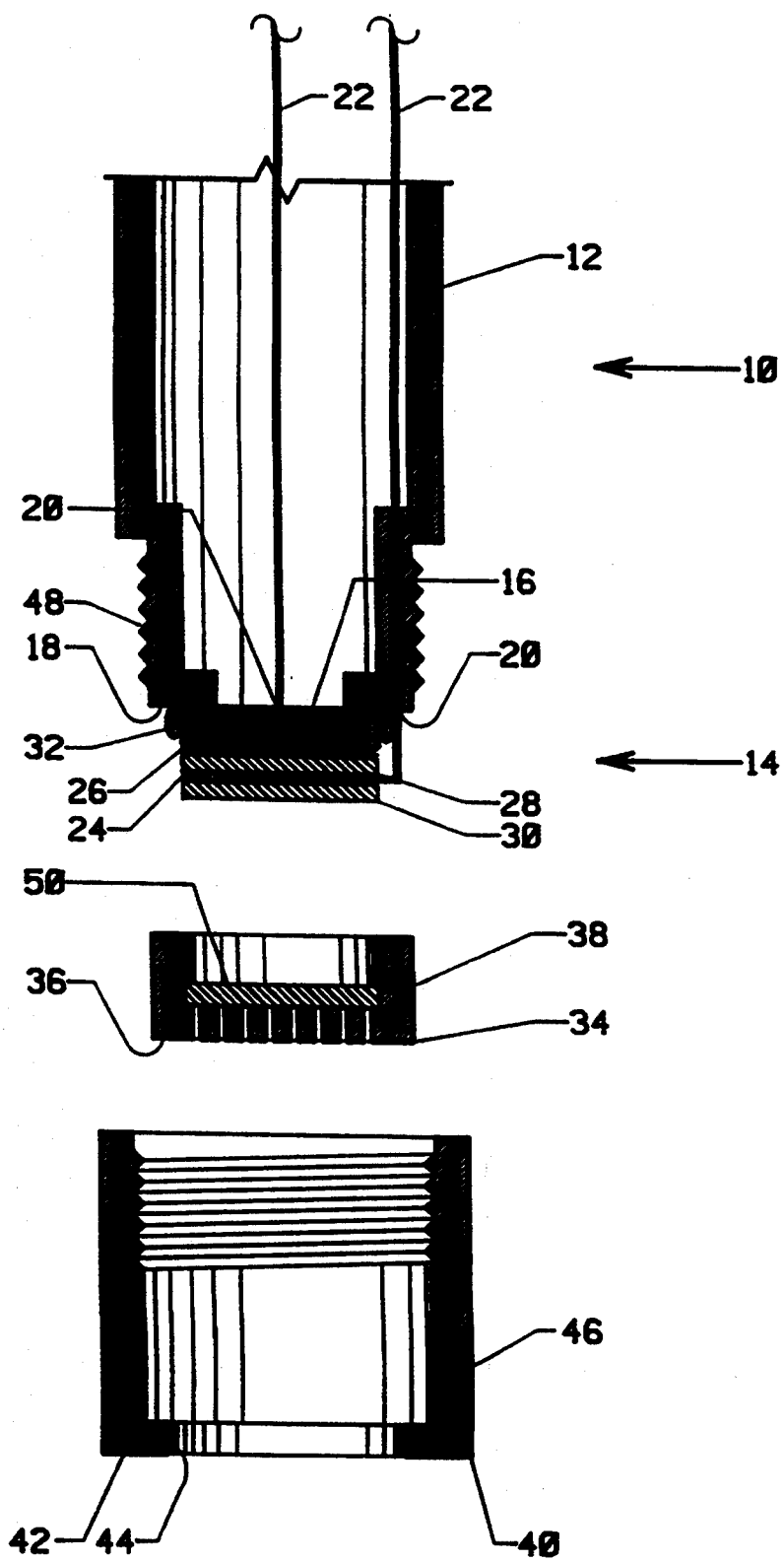
FIG. 1 is a cross-sectional view of a detector tip of an apparatus of this invention configured for operation in a galvanic, dissociative or a two-electrode amperometric mode.

The present apparatus for detecting a given compound are in each of these embodiments based upon a polymer film which acts in an electrolytic capacity. This film is comprised largely of a substantially inert, noncomplexing (non-participating) polymeric matrix which is appropriately suited to the environment of use, so that the film maintains its structural integrity in operation of the sensor apparatus while not interfering in the transport of ions from a working electrode to a counter electrode. The material forming the matrix can itself be electrically non-conducting or ion-conducting.

Suitable polymers may include, but are not limited to: poly(halo)olefins such as a poly(vinyl halide), including poly(vinyl chloride) and poly(vinyl fluoride), halogenated poly(vinyl chloride), chlorinated polyethylene, poly(vinylidene chloride), or poly(vinylidene fluoride); polyurethane; polystyrene; poly(ethylene terephthalate); chlorinated butyl rubber; isoprene/styrene/butadiene; styrene block copolymers, polyether ether ketone and the like. Useful polymers can also include copolymers of the foregoing materials, such as for example copolymers of poly(vinylidene chloride) with poly(vinyl chloride) or poly(methacrylate). For the process applications which are presently preferred, however, poly(vinylidene fluoride) is an especially preferred matrix polymer.

Because the base or matrix polymer is formed into a thin film and one convenient process for doing so is solvent casting, the polymer of choice for any given application may vary depending on the other ingredients and the finding of a common solvent for all. Other conventional techniques for thin film formation can also be employed, such as extrusion, spin casting, sputtering and heat pressing, or the film can be made by spraying the solution on a substrate with an airbrush. The best method presently known for preparing the polymer film for use in the apparatus of FIGS. 1-9 is solvent cast film formation, whereas in the apparatus of FIGS. 19, 20 and 21 the film may be applied to an interdigitated microsensor electrode array (hereafter, IME) by any of the known techniques for applying electroactive films to such devices, including dip coating, spin casting, spray painting or brush painting.

An essential ingredient of the polymer film in each of the various embodiments is a complexing agent for ionic species generated from a compound to be detected or for other ionic species found in the film (as, for example, from an electrolyte included in the film in a galvanic or amperometric mode). Materials which are commercially available as plasticizers have been found particularly suitable for use as complexing agents herein, although as suggested above it is not necessary in either the films including a compatible electrolyte material or not including such an added material, for the complexing agent to also plasticize the polymeric matrix in order for the electrochemical sensors incorporating these films to be effective. The complexing agent selected for a given application must however be highly compatible with and able to maintain a continuous phase throughout the polymeric matrix, and should further be suited to and compatible with the chemical and physical environment in which the film is to be employed, including being compatible with any other materials in the film and any species generated in operation of the apparatus.

Materials which are generally contemplated for use as complexing agents in the films of the present inventive sensing apparatus include the alkylene and polyalkylene glycol alkanoic diesters and alkylether esters of benzoic acid, terephthalic acid, phthalic acid, and adipic acid.

Preferred alkylene glycol alkanoic diesters have the formula:

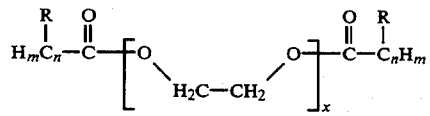

wherein X is a whole integer greater than or equal to 2 but less than or equal to 5, n is a whole integer greater than or equal to 4 but less than or equal to 12, and m=2n+1. Of this class of diesters, the compounds 2-ethylhexanoic tetraethylene glycol, 2-ethylheptanoic tetraethylene glycol, 2-ethylhexanoic triethylene glycol, 2-ethylheptanoic triethylene glycol, and mixtures thereof are thought to be especially useful. These diesters are commercially available from C. P. Hall, Inc., of Chicago, Ill., and are marketed under the trademark TegMeR ™. These materials preferably will comprise from about 30 to about 60 weight percent of the total weight of the polymer film.

An ether ester of terephthalic or adipic acid may also be used having the formula:

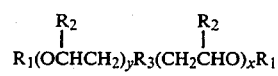

wherein $R_1$ is a phenyl radical or aliphatic hydrocarbon radical of the formula $C_aH_b$ wherein a is an integer of 1 through 8 inclusive and b is equal to $2a+1$; $R_2$ is either hydrogen or a methyl radical; $R_3$ is a terephthalate or adipate radical; X is 2, 3 or 4; and y is 2, 3 or 4, with x being preferably equal to y.

These terephthalic acid or adipic acid ether esters can be conventionally produced by known methods, for example a transesterification process disclosed in U.S. Pat. No. 4,620,026 to Siegel, wherein for example a dialkyl terephthalate and a mixture of polyalkylene glycols and polyalkylene glycol monoalkyl ethers are reacted with heating in the presence of a catalytic amount of calcium acetate. Methanol is collected overhead, and as the reaction proceeds, the polyalkylene glycols and polyalkylene glycol monoalkyl ethers are collected by distillation to leave the desired terephtalic acid ether esters.

The alkylene glycol monoethers and diethers are also thought to be generally suitable as complexing agents for the polymer films of this invention. Typical of such mono- and diethers are ethylene glycol dimethyl ether, triethylene glycol dimethyl ether, tetraethylene glycol dimethyl ether, poly(ethylene glycol) methyl ether, poly(ethylene glycol) tetrahydrofurfuryl ether and the like.

Additionally, the cyclic ethers including crown ethers, such as 12-crown 4, may also be used as complexing agents in the polymer films of the present invention.

Thus, generally preferred complexing agents are the poly(glycol) compounds, of which the poly(ethylene glycol) compounds are more preferred, especially poly(ethylene glycol) compounds selected from the group consisting of triethylene glycol and tetraethylene glycol ester, ether and terephthalate compounds.

In those embodiments of the invention which are configured to operate in a galvanic or amperometric mode, the polymer film further contains as an essential element an electrolyte material, such as an alkali metal salt, which is dissociable by the complexing agent in question. The electrolyte can in general be any conventional electrolyte which is compatible with the other materials in the film and with species encountered in the environment of use or generated in the use of the sensing apparatus, and which is suited in the same manner as the complexing agent to the physical conditions of the film's use, for example, temperature.

The electrolyte can be a compound of the formula $MX_a$. The M component is usually a metal and is preferably an alkali metal or an alkaline earth metal. Quaternary salts are also useful as the M component, exemplary quaternary salts including the ammonium and tetraalkylammonium salts, especially tetramethylammonium, tetrabutylammonium, and tetraphenylammonium compounds. Likewise, Group III metals which form soluble salts are useful and include, in the Lanthanide Series, cerium and neodynium. Further, the transition metals forming soluble salts including Zn, Cu and Pb are also useful as M components. The phosphonium salts such as tetraalkyl- and tetraarylphosphonium compounds, such as tetramethylphosphonium chloride or bromide, tetraphenylphosphonium chloride or bromide and trimethylphenylphosphonium chloride or bromide are likewise useful M components.

The X component can conventionally be a halide constituent, for example chloride, bromide, or iodide. In addition to the halides, anions of the salt can be selected from the following illustrative groups: nitrate, bisulfite, sulfite, sulfate, sulfide, tetraphenylborate, tetrafluoroborate, perchlorate, bicarbonate, methoxide, trifluoromethanesulfonate, acetate, hexafluorophosphate and the like. The selection of the M and X couple is, in all cases, such that the reduction potential of M is more positive than that for X. To insure good solubility, the M constituent of the $MX_a$ salt should have a Pauling's electronegativity less than that for X by at least 0.1 units.

Salt concentrations in those films which are configured to employ an added electrolyte material should at a minimum be sufficient to ensure adequate ion-conductivity therein, and it is generally desirable for any of these electrolyte salts to maximize the amount of electrolyte salt which can be uniformly distributed within the polymer film.

Figure 19:
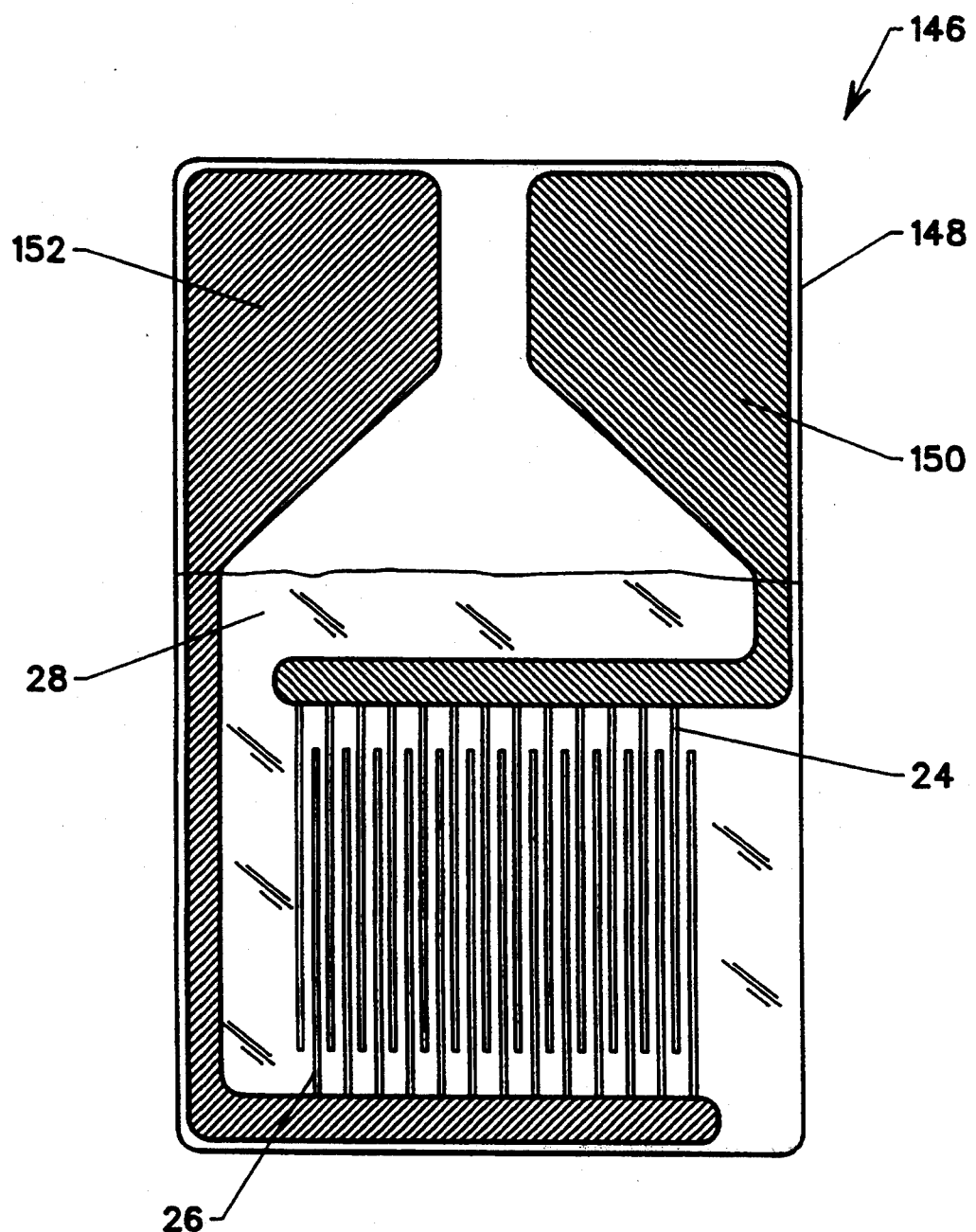
FIG. 19 is a perspective view of a most preferred polymer film and two-electrode arrangement to be employed in a sensor apparatus of the present invention, employing a commercially-available, interdigitated microsensor electrode array including two electrodes and having a polymer film of the present invention applied thereon.
Figure 20:
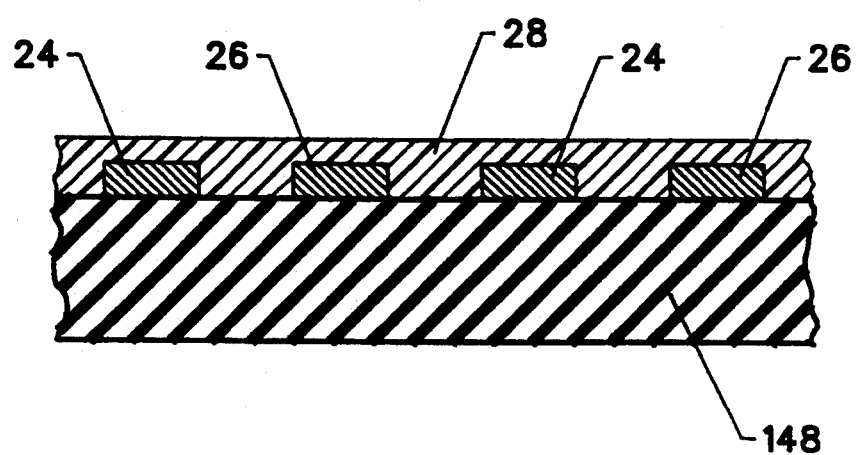
FIG. 20 is a partial cross-sectional view of the polymer film and interdigitated electrode arrangement shown in FIG. 19.
Figure 21:
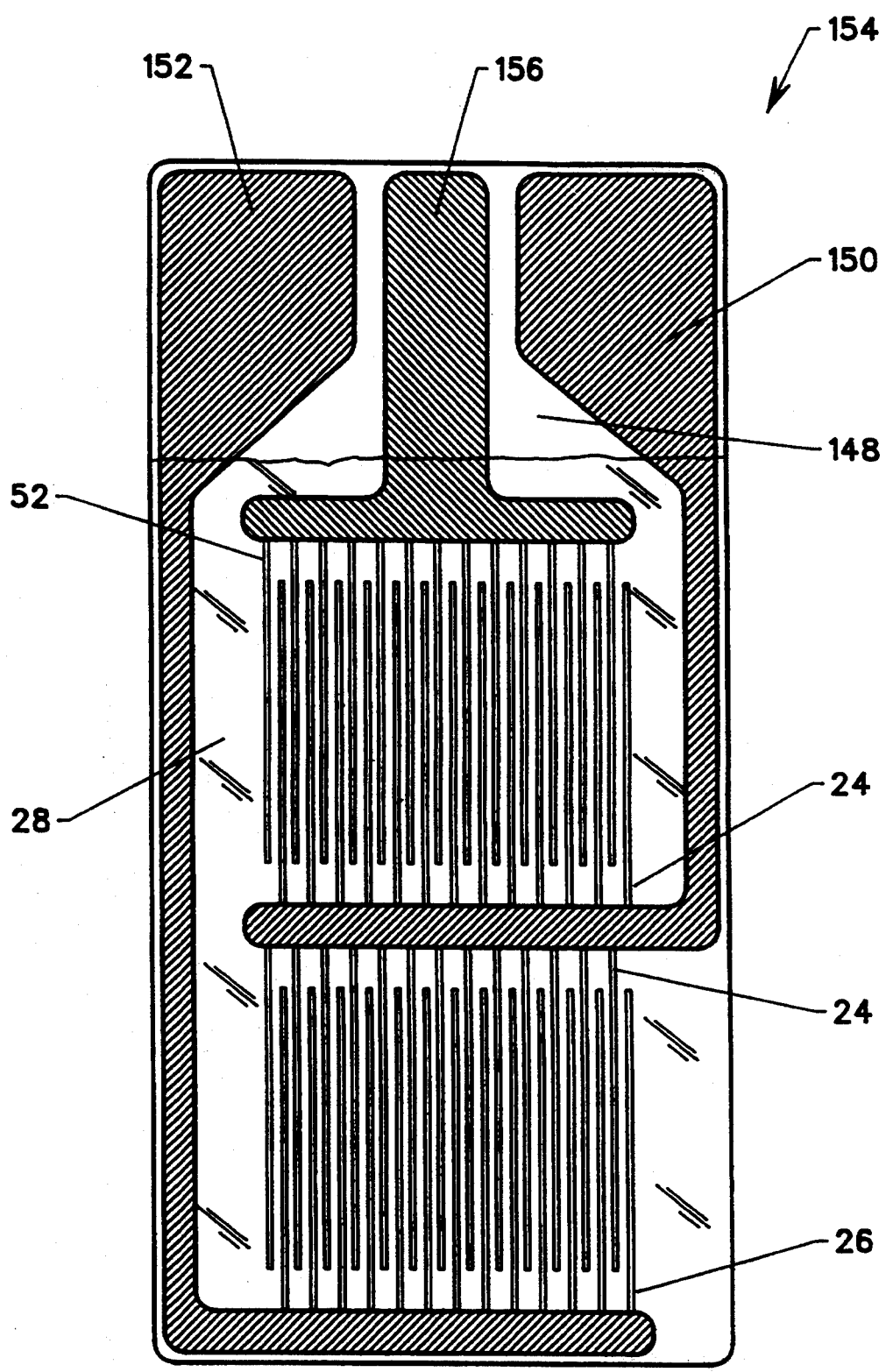
FIG. 21 is a perspective view of a most preferred polymer film and three-electrode arrangement, utilizing a commercially-available three electrode array.

Those skilled in the art will recognize that additional materials of a conventional nature, for example, stabilizers, pigments, polymer modifiers, processing aids, and the like, can optionally be included in the film in any of the dissociative, galvanic or amperometric arrangements and in either the sandwich-type electrode and film configuration depicted in FIGS. 1–9 or in the IME-based designs in FIGS. 19–21, where appropriate for purposes of processability, strength, durability, etc. and where such other materials are compatible and non-interfering.

Other properties of the films will obviously differ depending on whether the films are to be incorporated in the sandwich-type configuration of the embodiments of FIGS. 1–9, or are to be applied to IME's as per FIGS. 19–21. With respect to the former, the thickness of these films is desirably and preferably between about 1 to about 15 mils, with thicknesses between about 5 and about 10 mils being more preferred. The film's properties, including tensile strength, surface resistivity, water absorption, and density are all dependent on the amounts employed of an aforementioned complexing agent and salt, but it is only necessary with respect to these various film properties that the film be able to survive and function as a detector for a particular compound in the particular environment in which it is to be placed.

These films may suitably be made by a process which is more particularly described in the aforementioned U.S. Pat. No. 5,057,565 to Noding et al., but in general terms the ingredients for a particular polymer film of the present inventive apparatus are combined in a suitable vessel in an inert atmosphere, such as nitrogen, and (in the substantial absence of moisture) in an effective solvent for all of the ingredients. Several ether solvents, such as tetrahydrofuran, ester solvents, such as dipropylene glycol methyl ether acetate, and amide solvents, such as dimethylformamide, are excellent solvents of choice.

Once the ingredients are dissolved, the solution is placed in a flat-bottomed container and the container placed in a vacuum oven for a period of time sufficient to remove all solvent, resulting in a thin, whitish or colorless, opaque film. The film should be stored in an inert, dry atmosphere until used. In the dissolution step and the drying step, heat can be applied to aid in the dissolution or drying, but the temperature should not exceed the useful parameters of the polymer or any of its components.

Referring now to FIGS. 1–9, and more particularly to FIG. 1, a detector tip 10 of an apparatus of the present invention is illustrated as configured for operation in a dissociative, galvanic or two-electrode amperometric modes. Detector tip 10 comprises a generally cylindrical hollow extension tube 12. One end of extension tube 12 is preferably attached mechanically to a detector housing incorporating the power source (in the dissociative or amperometric modes), a current measurement apparatus and a switch for opening or completing the circuit at will (all not shown in FIG. 1), either adhesively or by mechanical connectors such as a bolted flange or screw threads, and the other end of extension tube 12 ends in the detecting assembly 14. Extension tube 12 is preferably fabricated from a nonconductive, readily moldable and workable material which is inert to the environment or environments in which the sensor apparatus is to be employed, for example, chlorinated poly(vinyl chloride) (CPVC) stock material, poly(vinylidene fluoride) or polyether ether ketone.

The detecting assembly 14 can be placed against an end wall 16 of the extension tube 12 which is formed as an integral part of the extension tube 12 (as shown). In the alternative, the end wall 16 can be a separate support piece for the detecting assembly 14 which is fitted securely into the extension tube 12 by interference fit or held in place adhesively, so that a shoulder 18 is defined with the end of extension tube 12. End wall 16 of extension tube 12 may thus be comprised of the same material as extension tube 12 or of a different material.

On one side of end wall 16 in the shoulder 18 and in the center of end wall 16 are drilled two electrode lead holes 20. The holes 20 should be only large enough to pass through the respective electrical lead wires 22 for the working electrode 24 and counter electrode 26. Electrodes 24 and 26 can be in various configurations attachable by heat-welding or some other means to lead wires 22, such as flat plates, spiral wound wire, foraminated flat electrodes of various shapes and other materials such as carbon cloth, with wire mesh discs being shown in FIG. 1.

Electrodes in the various embodiments of the present sensing apparatus can generally be comprised of any material which is electrically conductive and relatively inert to the reactions which occur thereon. Alternatively, the electrode can become involved in the reactions, but must be allowed to reverse and return to its initial state within a relatively short time in order to provide accurate readings and consumption. Typical electrode materials include carbon, platinum, nickel, gold, silver, palladium, and the like, with silver, platinum and gold or gold amalgam being preferred. Those skilled in the art will recognize that the various electrodes in these embodiments may be of the same or different materials, depending obviously on what mode of operation (i.e., dissociative, galvanic or amperometric) is contemplated for the apparatus.

As shown in FIG. 1, the two electrodes 24 and 26 are attached to electrical lead wires 22, usually by soldering or heat welding, lead wires 22 leading in turn to the electronics in the housing at their other end. The counter electrode 26 after connecting to one of the lead wires 22 is placed on end wall 16, then a polymer film 28 of the present invention is placed on the counter electrode 26, the working electrode 24 is placed on the film 28, and finally a barrier film 30 (which is selectively permeable to the compound of interest but which substantially prevents or restricts other, potentially interfering species in the fluid environment from contacting the working electrode 24) is placed over the working electrode 24 to form a complete detecting assembly 14.

To hold the detecting assembly 14 together, an O-ring 32 is placed around the end wall 16 and a protective set cap 34, having a foraminous end wall 36 and depending side wall 38, is in turn fit over the detecting assembly 14 and O-ring 32.

For protection from shock, dirt, moisture and other gross contamination, the detecting assembly 14 and protective set cap 34 are preferably overfit with a retainer cap 40. Retainer cap 40 includes an end wall 42 in which access hole 44 is found, and frown which an internally-screw-threaded side wall 46 depends. Side wall 46 in turn joins in threaded engagement with a matching threaded portion 48 of the extension tube 12. In order to provide further protection for the detecting assembly 14, one or more protective films 50 may optionally be placed inside set cap 34. These protective films 50 preferably are comprised of materials which will freely and easily let the compound to be detected through, but which prevent dirt, and substantially prevent or restrict moisture (in the form of liquid water/rain or water vapor, respectively) and other possibly deleterious material from contacting elements of the detecting assembly 14.

Thus, a combination of films 30 and 50 may be used which selectively transmit the species of interest while also protecting the electrodes 24 and 26 and the film 28 from gross interfering influences in the environment surrounding the detector tip 10 of the apparatus, influences which may include, for example, the presence of possibly interfering background materials. Or, barrier or protective films 30 or 50, respectively, may alone be used for their particular purposes in a detector tip 10. In most cases, it has been found sufficient to employ only a protective film 50, for example of Teflon TM polytetrafluoroethylene (E. I. DuPont de Nemours & Co., Inc.).

In operation of the apparatus of FIG. 1 in a dissociative mode, through an external power source (not shown) a voltage (for example, between 2 and 4 volts) is applied between the two electrodes 24 and 26.

Because no electrolyte is in the film 28 in the dissociative mode of the apparatus, the film is relatively non-conductive. However, upon contact of the film 28 with, for example, a vapor of hydrochloric acid, nitric acid, acetic acid or hydrofluoric acid, the dissolution of the acid vapor into the film 28 and the interaction of the acid and complexing agent contained in the film 28 cause a degree of dissociation of the acid into ions and increase the conductivity of the film 28. The resulting increased current flow between the electrodes 24 and 26 is measured by a conventional associated current measuring apparatus (not shown), and is related to the concentration of the acid vapor in the immediate environment.

In the galvanic mode, the external power source is omitted and the polymer film 28 is of the electrolyte-containing variety discussed extensively above, and the electrodes 24 and 26 are preferably of different materials.

The sum of the driving forces of the oxidation and reduction half-reactions at electrodes 24 and 26 produces a net spontaneous reaction and forces electrons to flow through an external electrical circuit. The current flow thus generated is related to the amount of the compound being oxidized or reduced and is observed or recorded (on an associated conventional current measurement apparatus) as the value of the change in the current as the electrochemical reaction proceeds.

To estimate the feasibility of detecting a certain compound in the galvanic mode of the present invention, the desired oxidation and reduction half-cell reactions are evaluated. In order to function in galvanic mode, the sum of the two half-cell reactions, $E_{(ox)} + E_{(red)} = E_{(cell)}$, must be positive. If $E_{(cell)}$ is negative, the reaction will be nonspontaneous and the compound's likelihood of detection is diminished. The standard reduction potentials differ from those in actual practice in the present invention because of differing environments, but the values give a rough estimate for use as a tool to determine the general ability of the present invention to operate in galvanic mode for detection of a given compound through oxidation or reduction to ionic species.

For example, for the detection of chlorine, the working electrode 24 can be of platinum and the counter electrode 26 can be of silver, with the electrolyte-containing polymer film 28 located therebetween. Under typical galvanic operating conditions, chlorine is reduced at the platinum working electrode 24 to form the chloride anion. As this half-reaction proceeds, a negative charge is built up near the working electrode. To compensate, the silver counter electrode 26 is oxidized to silver cation, which may be stabilized by combination with the corresponding anion of the electrolyte in the film 28.

In operation of the apparatus of FIG. 1 in a preferred two-electrode amperometric mode, an external power source is again present and the polymer film 28 contains an electrolyte salt. A potential is applied by an external power source between the reference/counter electrode 26 and the working electrode 24, and a steady baseline current established. As the compound to be detected permeates through the outer barrier film 30 and contacts the working electrode 24, a specific electrochemical reaction, determined by the applied potential and the given compound, takes place and causes an increase in the measured current flow between the electrodes 24 and 26. This increase in current is related to the concentration of the compound present. Thus, detection in the amperometric mode of compounds such as chlorine, sulfur dioxide, ozone, nitrogen dioxide, sulfuryl fluoride, phosgene, ammonia, perchloroethylene, tetrachloroethylene, methyl bromide, methyl chloride, silane, germane, arsine, benzene, toluene, ethylene and similar compounds can be accomplished.

Figure 2:
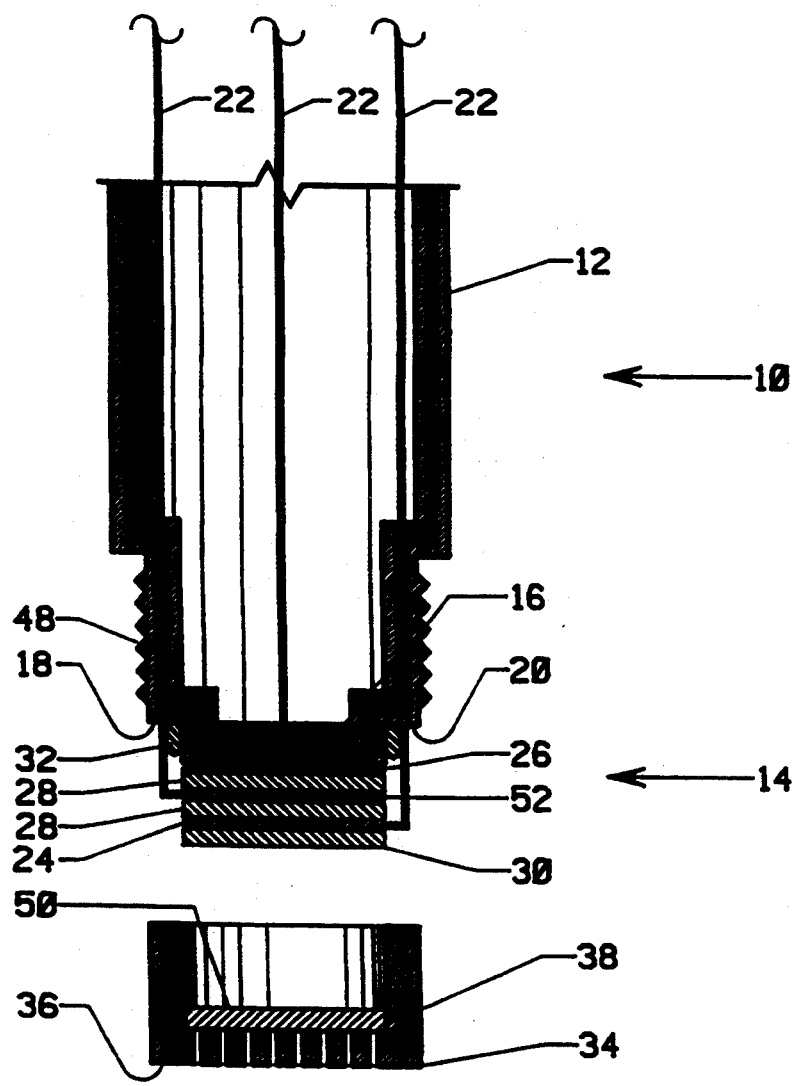
FIG. 2 is a cross-sectional view of a detector tip of an apparatus of this invention configured for operation in a three-electrode amperometric mode.
Figure 2:
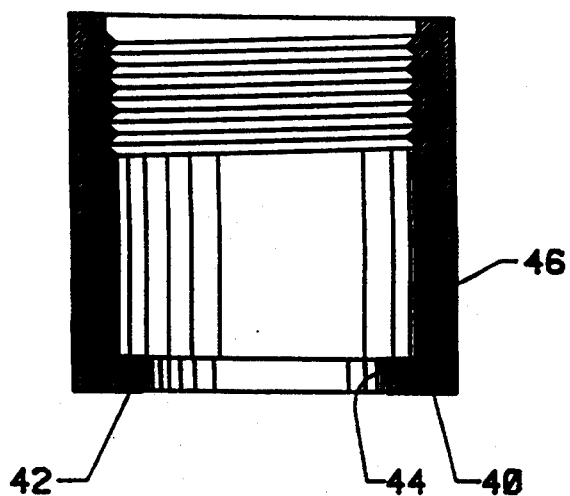

In another preferred embodiment of the present invention which is illustrated in FIG. 2, the polymer film-based electrochemical detector of this invention is configured for operation in a three-electrode amperometric mode. In this embodiment, the detector assembly tip 10 includes an extension tube 12 having three holes drilled therein for electrical leads 22; two of these three holes are in a shoulder 18 of the extension tube 12, while the third hole is defined in end wall 16. End wall 16 is again shown as being integrally-formed with the extension tube 12, although as with FIG. 1 the end wall 16 can be a separate piece which is interference-fitted in extension tube 12 or held in such position adhesively or by some other conventional means.

The three electrical leads 22 are respectively connected to a working electrode 24, a reference electrode 52 and a counter electrode 26. For the three electrode amperometric configuration, there are two electrolyte-containing polymer films 28 (which may be the same or different, provided the electrolytic salts dissociated in these films will not undergo an interfering reaction), the first being between the reference electrode 52 and the working electrode 24 and the second being between the reference electrode 52 and the counter electrode 26. Other elements can be as previously described in conjunction with the two-electrode amperometric embodiment of FIG. 1.

Figure 6:
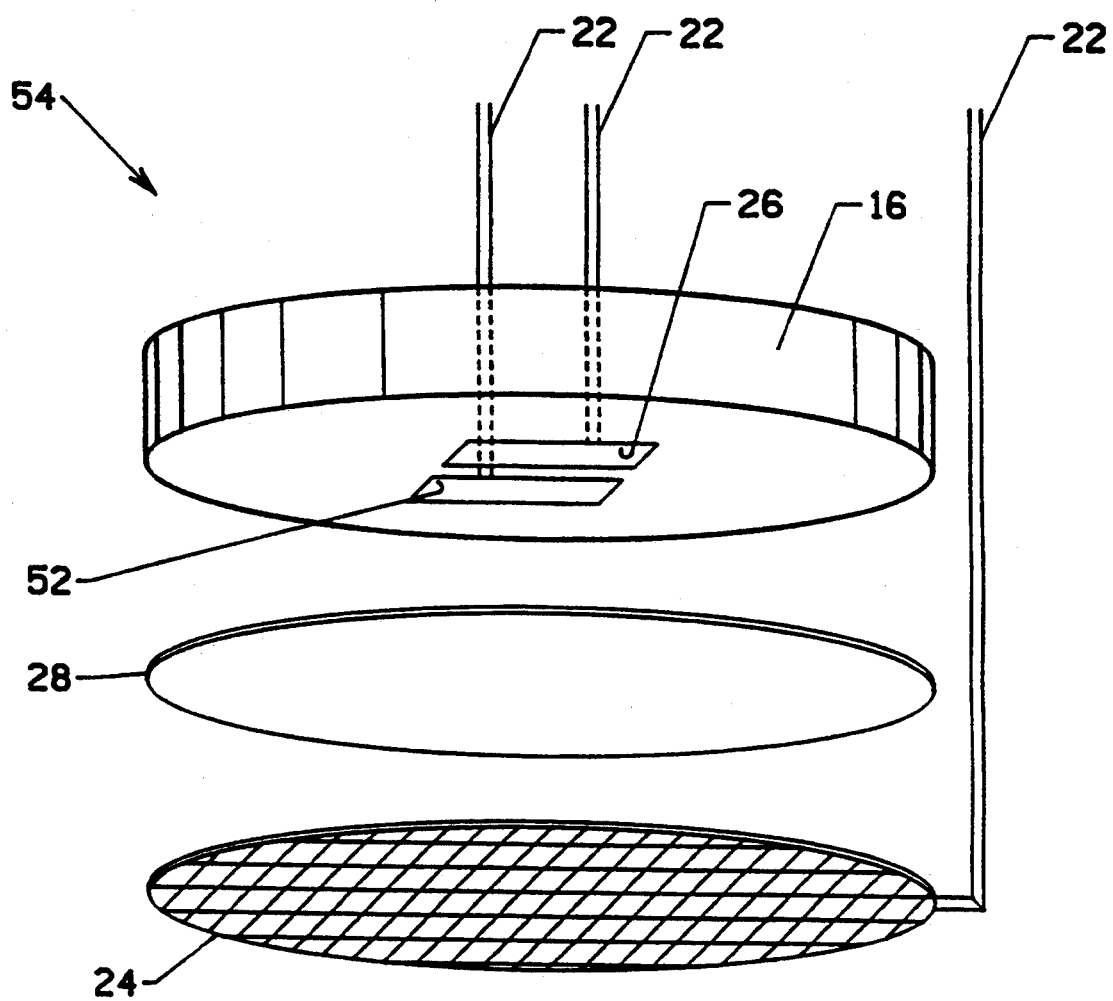
FIG. 6 is a partial perspective view of the electrode configuration in an alternate embodiment of the three-electrode amperometric arrangement of FIG. 2.

Considering now FIG. 6, the electrode configuration is shown for an alternate, more preferred embodiment of the three electrode amperometric arrangement of FIG. 2, other elements of the detector tip 10 having been omitted for clarity. In this embodiment 54, the reference and counter electrodes 52 and 26 are adhesively secured in end wall 16 in the form of coplanar strips of metal which are flush with the surface of the end wall 16 and in contact with a film 28. In practice, this construction can be accomplished by flattening the ends of respective lead wires 22 for electrodes 52 and 26, punching corresponding holes in end wall 16 (end wall 16 being made, again, of an electrically insulative, inert and durable material), adhesively securing the flattened ends in these holes by epoxy, for example, and polishing to achieve a smooth surface on the end wall 16 against which the film 28 can be placed. The working electrode 24 is in tile form of a conventional wire mesh, and is separated from the counter electrode 26 by a single film 28 as opposed to the two films 28 in FIG. 2. Wire mesh working electrode 24 has for this configuration (and for the configurations depicted in FIGS. 7, 8 and 9) preferably been flattened by pressure, so as to present as little hazard of puncturing film 28 as possible when assembled therewith in detecting assembly 14.

Figure 7:
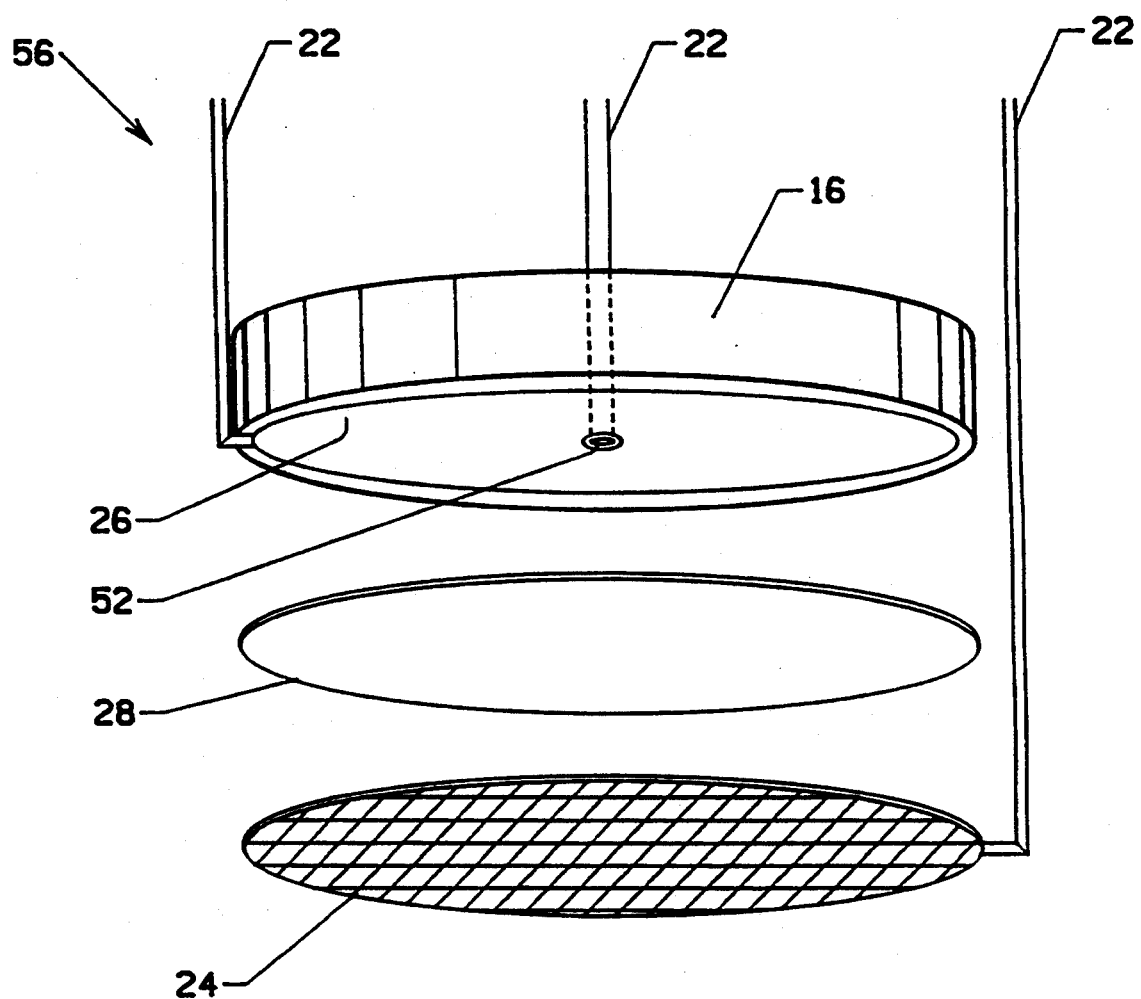
FIG. 7 is a partial perspective view of the electrode configuration in a second alternate embodiment of the three-electrode amperometric arrangement of FIG. 2.

In FIG. 7, still another embodiment of the three electrode amperometric arrangement is illustrated and designated as 56. In the embodiment 56, the reference and counter electrodes 52 and 26 are again coplanar, albeit in a different configuration. An electrical lead wire 22 is connected via heat-welding to a flat plate electrode 26, the flat plate electrode 26 having been glued with epoxy, for example, to the end wall 16. For reference electrode 52, the end of the corresponding electrical lead wire 22 is coated with an electrically insulative adhesive such as epoxy, a hole is punched through the plate electrode 26 and the coated lead wire 22 inserted through this hole to achieve a ring and disk arrangement familiar to those skilled in the art. The lead wire 22 can then be cut flush with the electrode 26, epoxied in place and polished to achieve a smooth surface on end wall 16. It will be appreciated that still other coplanar configurations of the electrodes 52 and 26 are possible and could be described herein for use in a sandwich-type configuration of one or more films 28 and associated working and counter, or working, counter and reference electrodes, but it is considered that those skilled in the art will be well able to conceive and reduce these other configurations to practice given the embodiments which have been described.

In still other embodiments, not shown, the working, reference and counter electrodes 24, 52 and 26 of a three-electrode amperometric detecting assembly 14 are all coplanar on end wall 16, whether in the manner of FIG. 6, FIG. 7 or some other configuration. It will also be appreciated that the two-electrode embodiments of the detecting assembly 14 could be made with coplanar working and counter electrodes 24 and 26 if desired.

Figure 8:
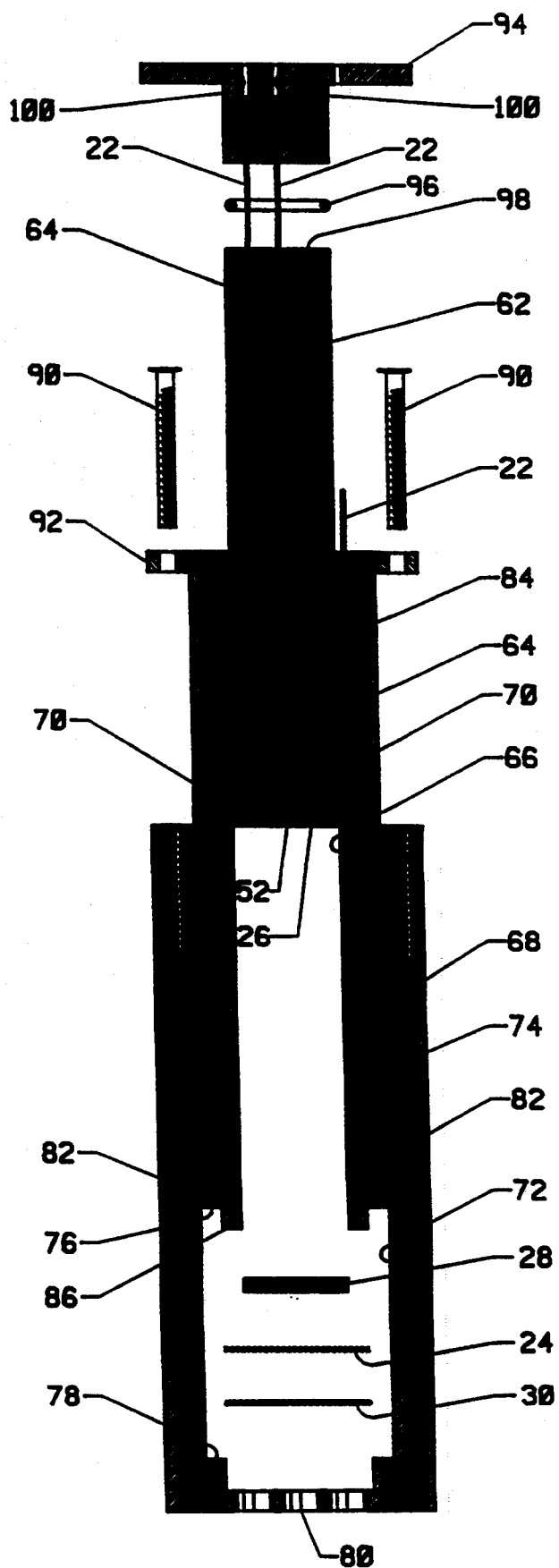
FIG. 8 is an exploded cross-sectional view of a preferred construction of a detector tip of an apparatus of the present invention.
Figure 9:
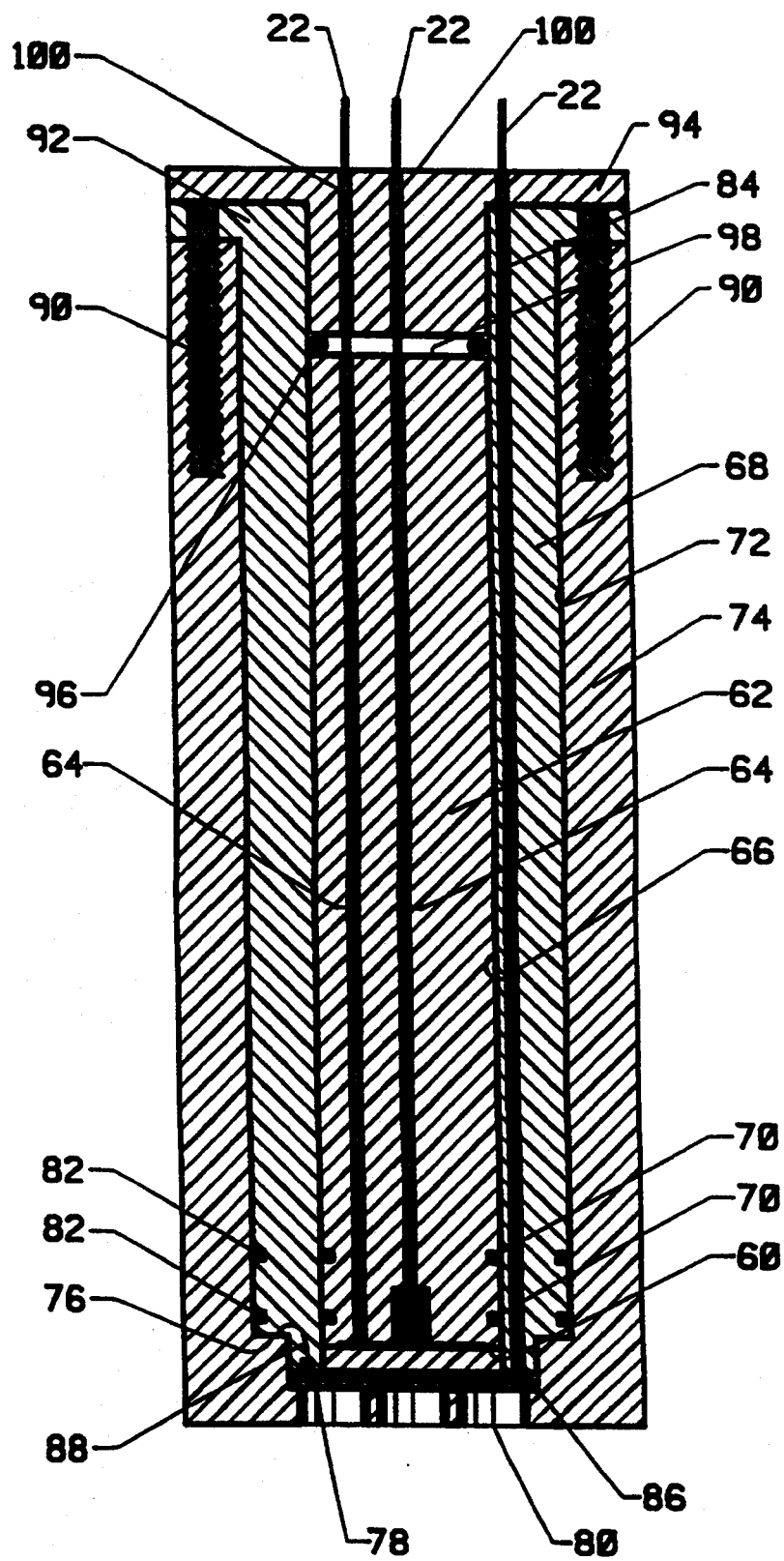
FIG. 9 is a cross-sectional view of the detector tip of FIG. 8, as assembled.

Turning now to FIGS. 8 and 9, an exploded cross-sectional view and an assembled cross-sectional view are respectively provided of a preferred construction 58 of a detector tip of an apparatus of the present invention.

In the embodiment 58, the counter and reference electrodes 26 and 52 are configured in a disk and ring arrangement on a first end 60 of a cylindrical first compression element 62, with the electrode 52 being formed as a disk element which has been potted to a separate electrical lead wire 22 rather than being an end of the lead wire 22 as in FIG. 7. Channels 64 are defined through the length of the element 62 for carrying the lead wires 22 for electrodes 52 and 26.

The first compression element 62 is slidably received within the barrel 66 of a cylindrical second compression element 68, with O-rings 70 being defined about the circumference of first compression element 62 for maintaining a seal with the barrel 66 of the second compression element 68.

Second compression element 68 in turn is slidably received within the barrel 72 of an outer protective shell member 74, with second compression element 68 and outer protective shell member 74 defining corresponding shoulder portions 76 and 78, respectively, for retaining the second compression element 68 within outer protective shell member 74 and for allowing a degree of compression between second compression element 68, a perforated first end 80 of the shell member 74 adjacent shoulder portion 78, and a flat wire mesh working electrode 24 and barrier film 30 positioned (in this order) between the second compression element 68 and the first perforated end 80 of shell member 74.

O-rings 82 are defined about the circumference of second compression element 68 for maintaining a seal with the barrel 72 of outer shell member 74. An electrical lead wire 22 in a channel 84 defined along the length of the second compression element 68 leads to a wire ring 86 which is placed or embedded in a first end 88 of the compression element 68, the wire ring in turn electrically contacting the wire mesh working electrode 24 at the electrode 24's circumference when the second compression element 68, electrode 24, barrier film and shell member 74 are assembled in compression.

This assembly is achieved by means of preferably finely-threaded screws 90 passing through a flanged second end portion 92 of the second compression element 68 and into the outer shell member 74 parallel to the longitudinal axis of cylindrical second compression element 68; by virtue of this construction the degree of compression of the barrier film 30 and working electrode 24 at their circumference can be finely adjusted merely by tightening or loosening the screws 90.

An electrolyte-containing polymer film 28 of the present invention is in the barrel 66 of the second compression element 68 adjacent its first end 88, and in position to be compressed by the first compression element 62 at its first end 60 against the working electrode 24. This is accomplished in the general manner described in the preceding paragraph, by joining a flanged cap 94 to the flanged second end portion 92 of second compression element 68 through preferably finely threaded screws (not shown, and offset from the screws 90). Flanged cap 94 extends into the barrel 66 and presses against a resilient compression member 96, which member 96 can preferably be an O-ring as shown, or which can be a spring for example. Resilient compression member 96 is positioned between the cap 94 and a second end 98 of the first compression element 62, whereby as the screws joining the cap 94 to the flanged second end portion 92 of the second compression element 68 are tightened or loosened, the pressure transmitted through the member 96 against the second end 98 of first compression element 62 and in turn against the film 28 and detecting assembly 14 is incrementally increased or decreased. Channels 100 are defined through the flanged cap 94 for each of the electrical lead wires 22 from the electrodes 24, 26 and 52.

In the various embodiments of FIGS. 1, 2, 6 and 7, the electrode leads 22 are connected to an electronic working circuit which preferably operates in true potentiostatic fashion. An exemplary working circuit for a three-wire amperometric version of the apparatus is shown, for example, in schematic fashion in FIG. 3 and identified generally as 102; those skilled in the art will, however, again be well able to construct analogous circuits adapted to the various embodiments, modes of operation and electrochemical techniques contemplated herein.

Figure 3:
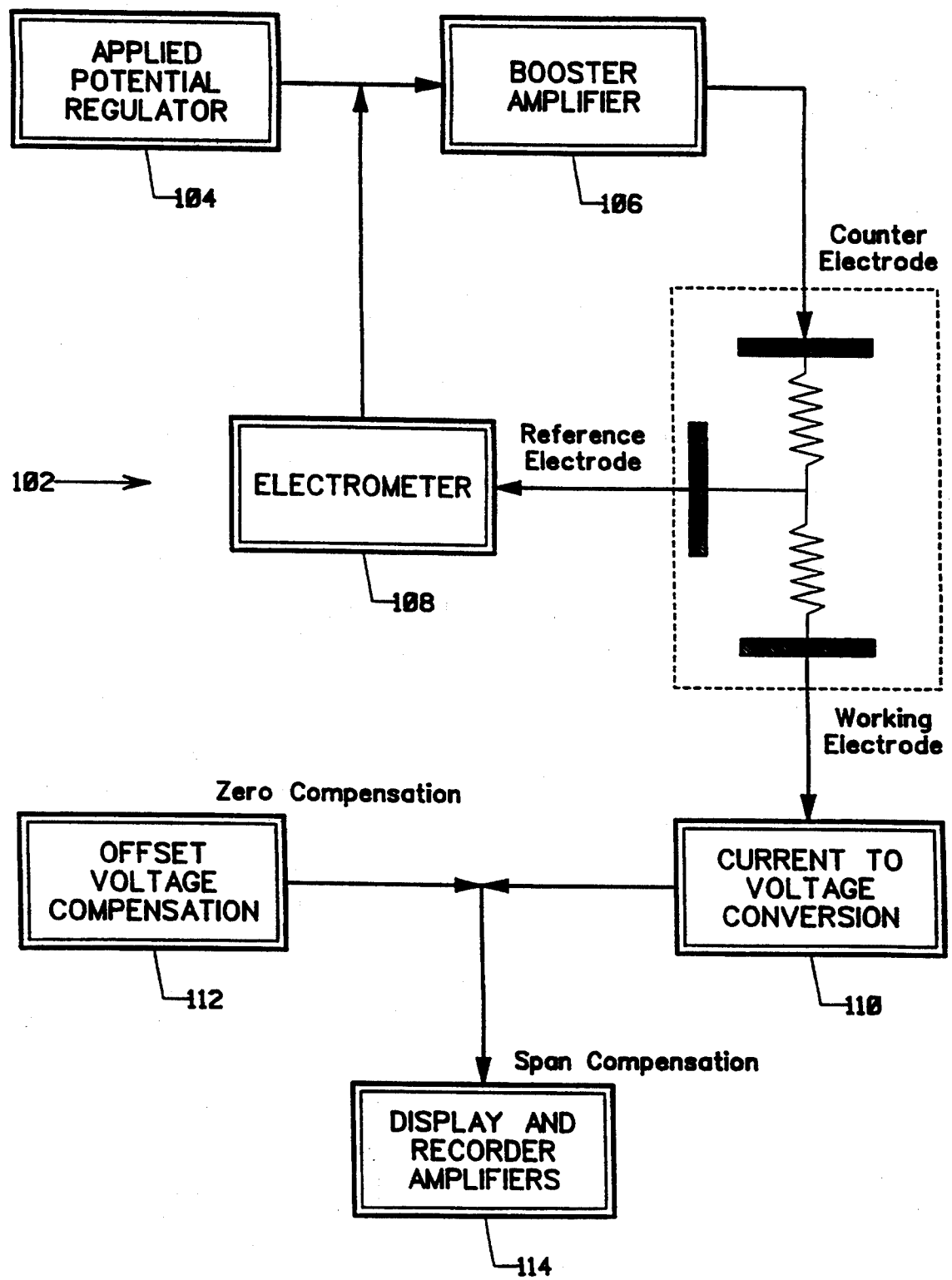
FIG. 3 is a block circuit diagram of an electronic working circuit useful in an amperometric mode of operation.
Figure 4:
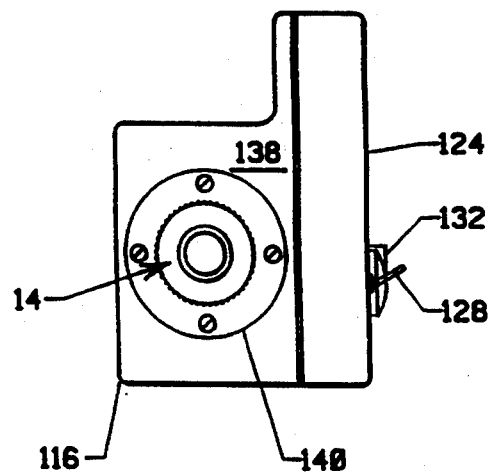
FIG. 4 is an end view of one embodiment of this invention in portable hand-held operational configuration for use in ambient atmosphere monitoring.
Figure 5:
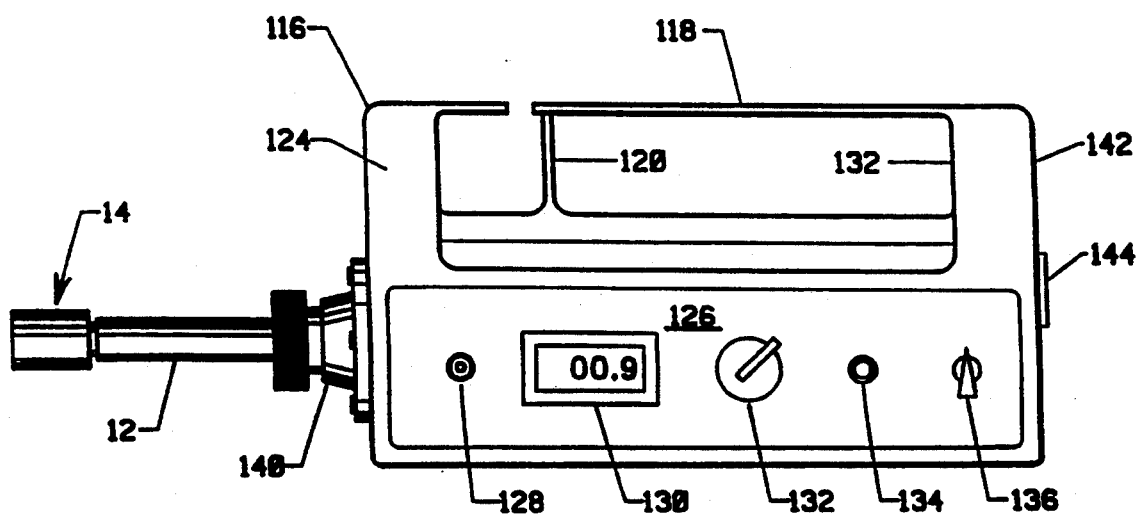
FIG. 5 is a side view of one embodiment of this invention in portable, hand held operational configuration for use in ambient atmosphere monitoring.

The electronic working circuit 102 mounted on a custom printed circuit card supplies signals to a digital readout device and recorder device output connector, not shown in FIG. 3. A power switch, recorder jack, zero control and span adjustment controls are mounted on a custom user interface panel on one side of an instrument case shown generally in FIG. 5 for ambient atmosphere monitoring, detection of fugitive emissions or like uses. The applied potential regulator 104 with booster amplifier 106 drives the counter electrode 26. Reference electrode 52 and electrometer 108, which may be an operational amplifier with high impedance to minimize current flow through the reference electrode 52, work as a control loop to assure the desired applied potential is maintained between the reference and working electrodes, 52 and 24, respectively.

As a compound to be detected contacts working electrode 24, an electrochemical reaction of the compound to be detected occurs, resulting in more current. The counter electrode 26 is driven to maintain the potential difference between the working electrode 24 and the reference electrode 52. A measurement of current at the working electrode 24 is related to the concentration of the compound to be detected.

In this embodiment, it has been chosen for convenience to convert the current to voltage with a current to voltage converter 110. Voltage is corrected to zero with an offset voltage compensator 112. The output is directed to display and recorder amplifiers, generally shown at 114 for appropriate display and recorder devices, not shown, of a conventional nature.

Each of the components in electronic working circuit 102 may have one or more components and be a separate or interconnected electronic circuit which are known to skilled instrument designers. The potentiostat which has been described briefly herein is a well known voltage control circuit, as demonstrated in Bard and Faulkner, "Electrochemical Methods: Fundamentals and Applications", John Wiley & Sons, New York, 1980, p. 20 561–567.

The working circuit 102 can be powered from sources which provide positive 12–16 volts D.C., such as an internal 12 volt battery, an external 12-volt battery, a 110-volt AC adapter, or an automotive battery supply of 12-volt D.C. as appropriate or available using power conditioning circuits. Internal power conditioning components are preferably conventional integrated circuits which determine the positive voltage source used. A voltage inverter produces an unregulated negative D.C. voltage. Then both the unregulated positive and negative D.C. voltages are regulated by integrated circuits producing regulated ±7.5 volts D.C., or a total voltage of 15 volts across the leads to the booster amplifier 106. The foregoing is only one conventional method known to the skilled practitioner to produce a regulated power supply. Each of the components in this embodiment are low power integrated circuits designed for specific applications and are conventionally known.

Electronic circuitry such as described above is used in a variety of applications including fixed mount process transmitters, fixed mount environmental monitors and portable, hand-held monitors. An example of this last-mentioned application is (again) shown in FIGS. 4 and 5, wherein a portable, hand-held housing 116 is useful to contain electronic working circuit 102 (not shown per se in FIGS. 4 and 5).

Housing 116 functions to protect the electronic components of the present sensor apparatus, and can be constructed of any suitably durable material which does not interfere with the electronics, such as polypropylene, acrylonitrile-butadiene-styrene, high impact polystyrene, reinforced fiberglass-filled polyamide and the like.

Housing 116 comprises an integral handle 118, supported by front handle support 120 and rear handle support 122. Side panel 124 contains instrument panel 126 wherein a power switch 128, output display 130, zero adjustment dial 132, output signal recorder lack 134 and span adjustment control 136 are found. Attached to a front wall 138 of the housing 116 is a LEMO TM brand connector 140, which provides a quick connection of the leads from the detecting assembly 14 through extension tube 12. In a back wall 142 of housing 116 is located a power connector 144, which is of a conventional configuration for connecting a power cable plug from an automotive 12 volt D.C. battery, 110 volt A.C. adapter or the like. While housing 116 is shown as a generally rectangular structure having a handle on top, the configuration of housing 116 is limited only by the practical requirements of containing the electronic components of the detector apparatus of the present invention.

Turning now to FIGS. 19, 20 and 21, most preferred polymer film and electrode arrangements are shown which respectively employ commercially-available, interdigitated microsensor electrode arrays including two (i.e., working and counter) or three (i.e., working, counter and reference) electrodes and having polymer films of the present invention applied therein. These IME's are commercially available from various sources, e.g., EG&G Princeton Applied Research, Princeton, N.J. 08543 (a public unit of EG&G, Inc., Wellesley, Mass.), Silica Source Technology Corp., Tempe, Ariz., and are conventionally fabricated by integrated circuit fabrication techniques to produce arrays having areas ordinarily on the order of from one to several square millimeters, with individual digits and interdigit spacing being typically microns in dimension.

An exemplary interdigitated, two-electrode array and polymer film arrangement 146 in FIGS. 19 and 20 employs, in a two electrode dissociative mode on an insulating substrate 148 and in an electrical circuit: interdigitated working and counter electrodes 24 and 26 connected to lead wires (not shown here) via respective pad portions 150 and 152; an external power source (not shown) for applying a voltage between the electrodes 24 and 26; a current measurement means (not shown, but being comprised of conventional circuitry and elements) having the capability of measuring nanoamps and picoamps of current (as opposed to the microamps of current seen in the Examples below with the sandwich-type configurations of FIGS. 1–9); and a micronsthick polymer film 28 of the present invention which has been applied, for example, by spray-coating of the IME with a solution of the polymeric matrix material and a suitable complexing agent.

An optional resistance temperature detector, such as a conventional platinum serpentine resistor, is preferably incorporated on the substrate 148 for applying an appropriate temperature correction to the response of the apparatus in a given environment, or a separate temperature measuring device may be employed in conjunction with the inventive apparatus for determining and applying an appropriate correction. Preferably also, in an alternate embodiment a humidity sensor of conventional design is employed on the substrate 148 where the response of the sensor apparatus to a given species is variable dependent on the water content of the sensing environment, as for example, in the ambient detection of chlorine, although here too a separate humidity detector could be employed.

In a galvanic version of the arrangement 146 as in the two electrode galvanic arrangement described above in conjunction with FIG. 1, the polymer film 28 includes a compatible electrolyte material, the electrodes 24 and 26 are comprised of different materials and the external power source is omitted. A two electrode amperometric apparatus incorporates an electrolyte material into the film 28, and employs an external power source to apply a potential between the reference/counter electrode 26 and the working electrode 24.

In FIG. 21, in a three electrode amperometric apparatus 154, interdigitated working, counter and reference electrodes 24, 26 and 52, respectively, are provided on the substrate 148 and connected to lead wires via corresponding pad portions 150, 152 and 156. The remaining elements are as described in the preceding two paragraphs in conjunction with the two electrode amperometric apparatus.

Various dissociative, galvanic and amperometric sensor apparatus have been described herein. Those skilled in the art will appreciate that these apparatus will be useful in a variety of circumstances, and that each of these modes and apparatus may be particularly suited for the detection of certain compounds and certain applications. The selection of an appropriate mode of operation and configuration for any given application is considered to be within the abilities of those skilled in the art, particularly given the description above of useful applications and given the examples which follow.

Further, while the foregoing description has focused on the use of a single sensor assembly to detect a single selected species, those skilled in the art will readily appreciate that a plurality of the above-described assemblies could be employed together for detecting a number of species in a stream or environment such as a vent stack containing or potentially containing a mixture of species of interest, and that the IME-based versions when coupled with a microprocessor or like data processing means lend themselves particularly well to this type of application.

The present invention is more particularly illustrated by the examples which follow:

EXAMPLE 1

Figure 10:
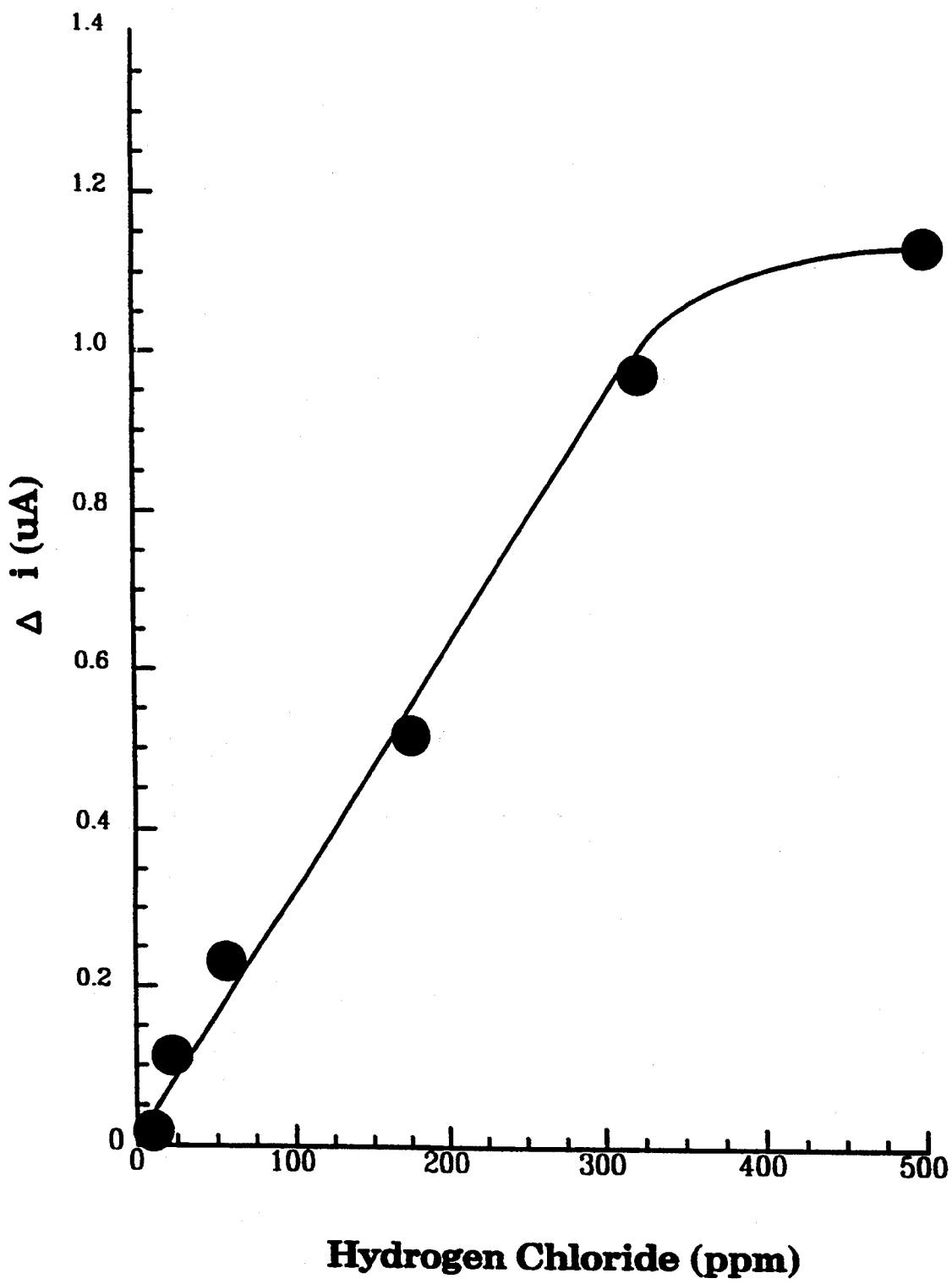
FIG. 10 is a calibration curve for one embodiment of the invention as used in a dissociative mode to detect hydrogen chloride.

An apparatus was constructed for this Example in a configuration as shown in FIG. 1. A film was prepared for use therein which contained 46 weight percent of poly(vinyl chloride), 46 weight percent of TegMeR TM 804 tetraethylene glycol di-(2-ethylhexanoate) and 8 weight percent of epoxidized soybean oil as a UV stabilizer (for the poly(vinyl chloride)). These materials were combined with dimethylformamide and solvent cast, with the dimethylformamide being evaporated in a vacuum oven to produce the desired 15 mil thick film. A 0.5 inch diameter film sample was placed between a platinum working electrode and a platinum counter electrode in the apparatus and a potential of 2 volts direct current (D.C.) was applied between the electrodes, producing a baseline, anodic current of less than 1 microamperes. The film was contacted in a flow cell with various concentrations of HCl gas in nitrogen, using commercially-available gas sources (i.e., bottles or generators) and gas blending equipment to achieve these concentrations. As the HCl concentration increased, the measured current also increased, creating the calibration curve shown in FIG. 10. As can be seen, the detector response from about 5 ppm HCl up to about 300 ppm HCl was essentially linear. The measurements reflected in FIG. 10 are provided in Table 1 as follows:

TABLE 1

| PPM of HCl | Change in Measured Current (uA) |
|---|---|
| 13 | 0.03 |
| 25 | 0.20 |
| 58 | 0.23 |
| 175 | 0.52 |
| 325 | 0.98 |
| 500 | 1.13 |

EXAMPLE 2

An apparatus was constructed for this Example in a galvanic configuration using a 15 mil film disk (about 0.5 inches in diameter) of 46 weight percent poly(vinyl chloride), 23 wt. percent lithium chloride, weight percent TegMeR TM 804 tetraethylene glycol di-(2-ethylhexanoate) and 8 weight percent of epoxidized soybean oil prepared as described in Example 1. This film was placed between a platinum working electrode and a silver counter electrode, and the two leads for these electrodes were connected to a voltmeter through a resistor to convert current to voltage readings. Various concentrations of chlorine in air were prepared and allowed to contact the sensor via the apparatus and procedure of Example 1, and voltage measurements were taken at these various concentrations. The results obtained are as shown in Table 2.

TABLE 2

| PPM of Cl$_2$ | Change in Voltage (mV) |
|---|---|
| 5 | 30 |

TABLE 2-continued

| PPM of $Cl_2$ | Change in Voltage (mV) |
|---|---|
| 10 | 55 |
| 20 | 115 |
| 30 | 180 |
| 42 | 250 |

Figure 11:
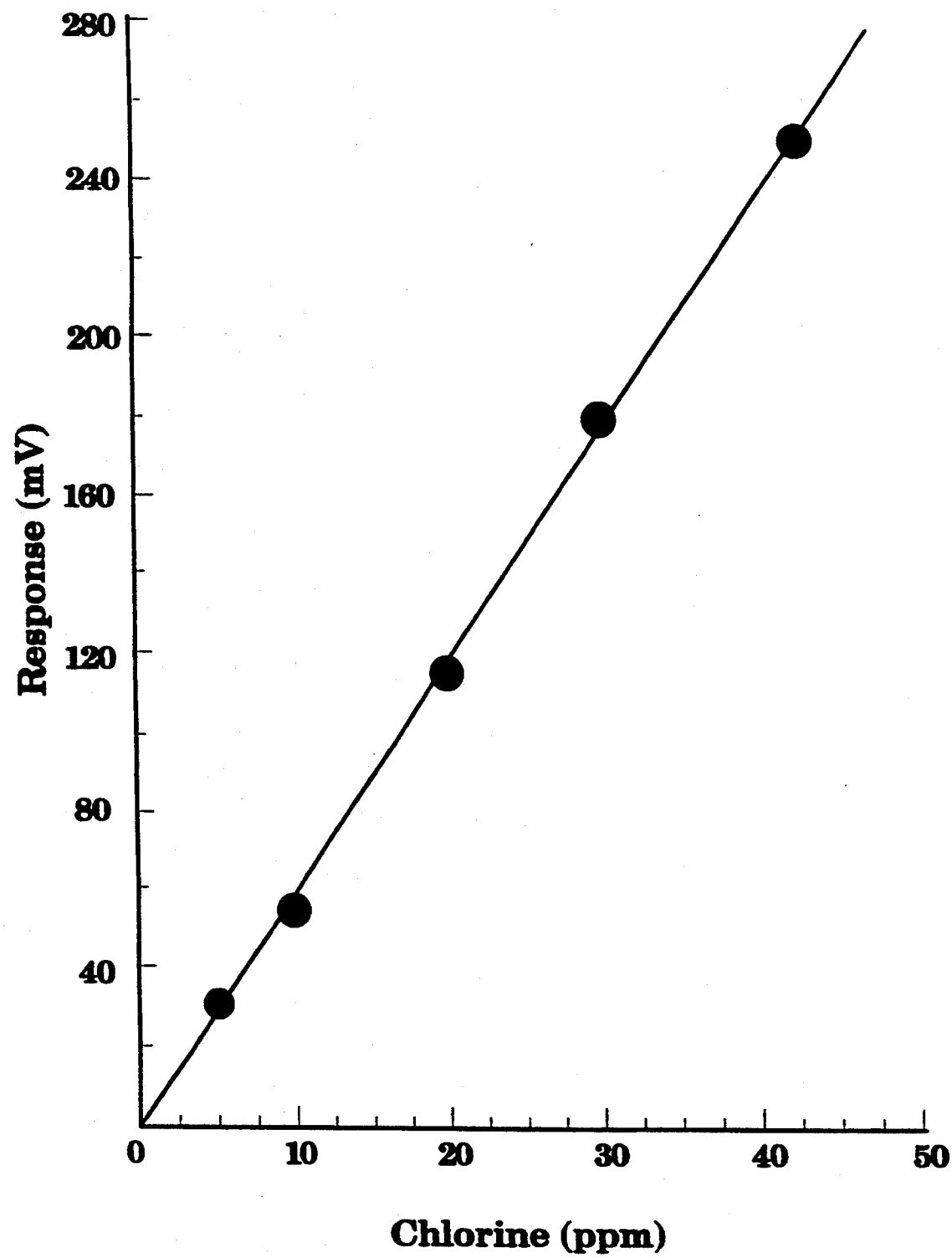
FIG. 11 is a calibration curve for one embodiment of the invention as used in a galvanic mode to detect chlorine.

The corresponding calibration curve in FIG. 11 shows the detector's response was essentially linear from about 5 ppm of chlorine through 42 ppm of chlorine.

EXAMPLE 3

Figure 12:
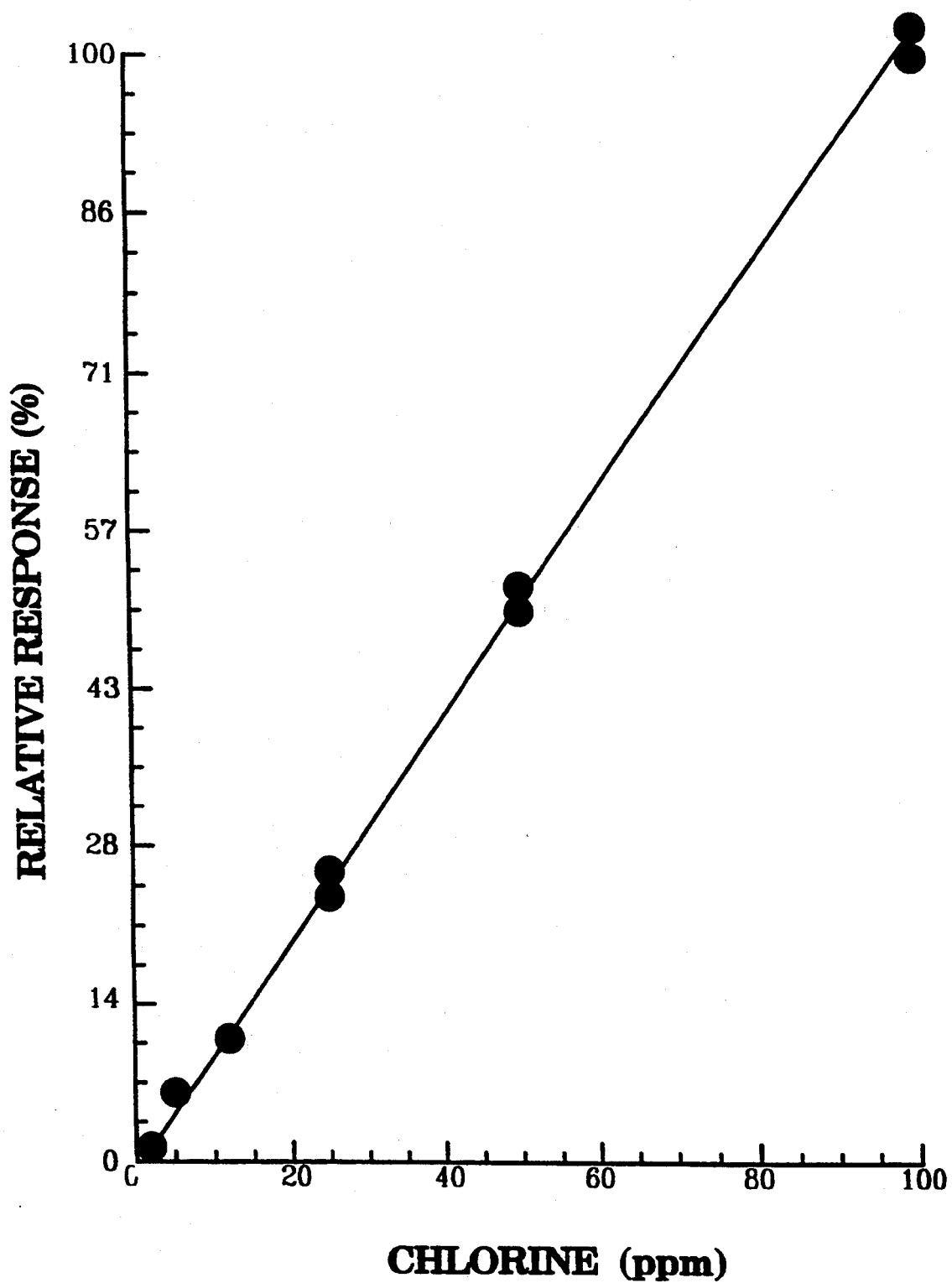
FIG. 12 is a calibration curve for one embodiment of the invention as used in an amperometric mode to detect chlorine.

An apparatus of the present invention was assembled as in FIG. 2, employing two 0.5 inch diameter polymer films containing 46 weight percent of poly(vinyl chloride), 23 weight percent of TegMeR ™ 804 material, 23 weight percent lithium chloride and 8 weight percent of epoxidized soybean oil. One such film was placed between a platinum working electrode and a silver reference electrode and the other was placed between the silver reference electrode and a platinum counter electrode. The electrode leads were connected to a working circuit like that shown in FIG. 3. A bias potential of a positive 0.25 volts was applied to the working electrode with respect to the reference electrode. The detecting assembly was contacted (in the manner of previous examples) with various concentrations of chlorine in air, resulting in the measurements in Table 3 and the calibration curve of FIG. 12.

TABLE 3

| PPM Of $Cl_2$ | Change in Relative Response (Pct.) |
|---|---|
| 0 | 0 |
| 5 | 7 |
| 12 | 11 |
| 25 | 23 |
| 25 | 26 |
| 50 | 50 |
| 50 | 53 |
| 100 | 98 |
| 100 | 102 |

EXAMPLE 4

Figure 13:
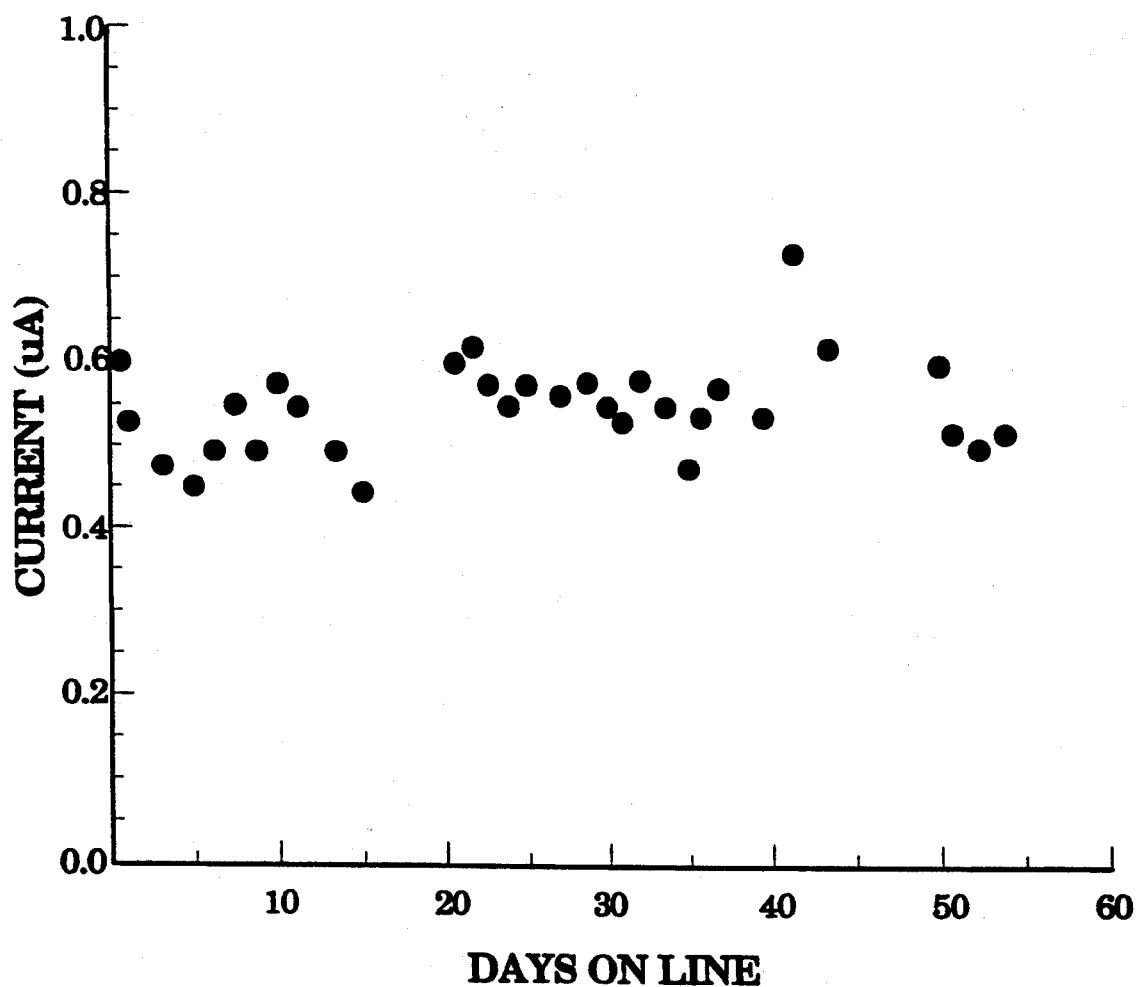
FIG. 13 is a stability diagram illustrating the detection of 5 ppm chlorine for one embodiment of the invention in an amperometric mode.

A three-electrode amperometric set up was used for this Example as in Example 3, with platinum working and counter electrodes, a silver reference electrode and with two 0.5 inch diameter polymer films comprising 64 weight percent of poly(vinyl chloride), 32 weight percent of the TegMeR ™ 804 material, 3 weight percent of lithium chloride, and 1 weight percent of diglycidyl ether of bisphenol A (a stabilizer commercially available under the tradename D.E.R. 331 from The Dow Chemical Company). A barrier film of vinylidene chloride-methyl acrylate copolymer was included to minimize sensor exposure to oxygen and water. The apparatus thus constructed was periodically exposed to 5 ppm of chlorine in ambient air over 52 days. The performance of the sensor over this period is indicated by the data summarized in Table 4 and shown in FIG. 13.

TABLE 4

| Days on Line | Change in Current (uA) |
|---|---|
| 1 | 0.60 |
| 2 | 0.52 |
| 4 | 0.46 |
| 5 | 0.44 |
| 6 | 0.48 |
| 7 | 0.54 |
| 9 | 0.49 |
| 10 | 0.56 |
| 12 | 0.53 |
| 13 | 0.49 |
| 15 | 0.43 |
| 21 | 0.60 |
| 22 | 0.63 |
| 23 | 0.58 |
| 24 | 0.53 |
| 26 | 0.58 |
| 28 | 0.55 |
| 29 | 0.57 |
| 30 | 0.52 |
| 31 | 0.51 |
| 32 | 0.57 |
| 35 | 0.52 |
| 36 | 0.46 |
| 37 | 0.52 |
| 38 | 0.56 |
| 39 | 0.51 |
| 41 | 0.73 |
| 43 | 0.61 |
| 50 | 0.60 |
| 51 | 0.50 |
| 52 | 0.47 |
| 54 | 0.50 |

EXAMPLE 5

Figure 14:
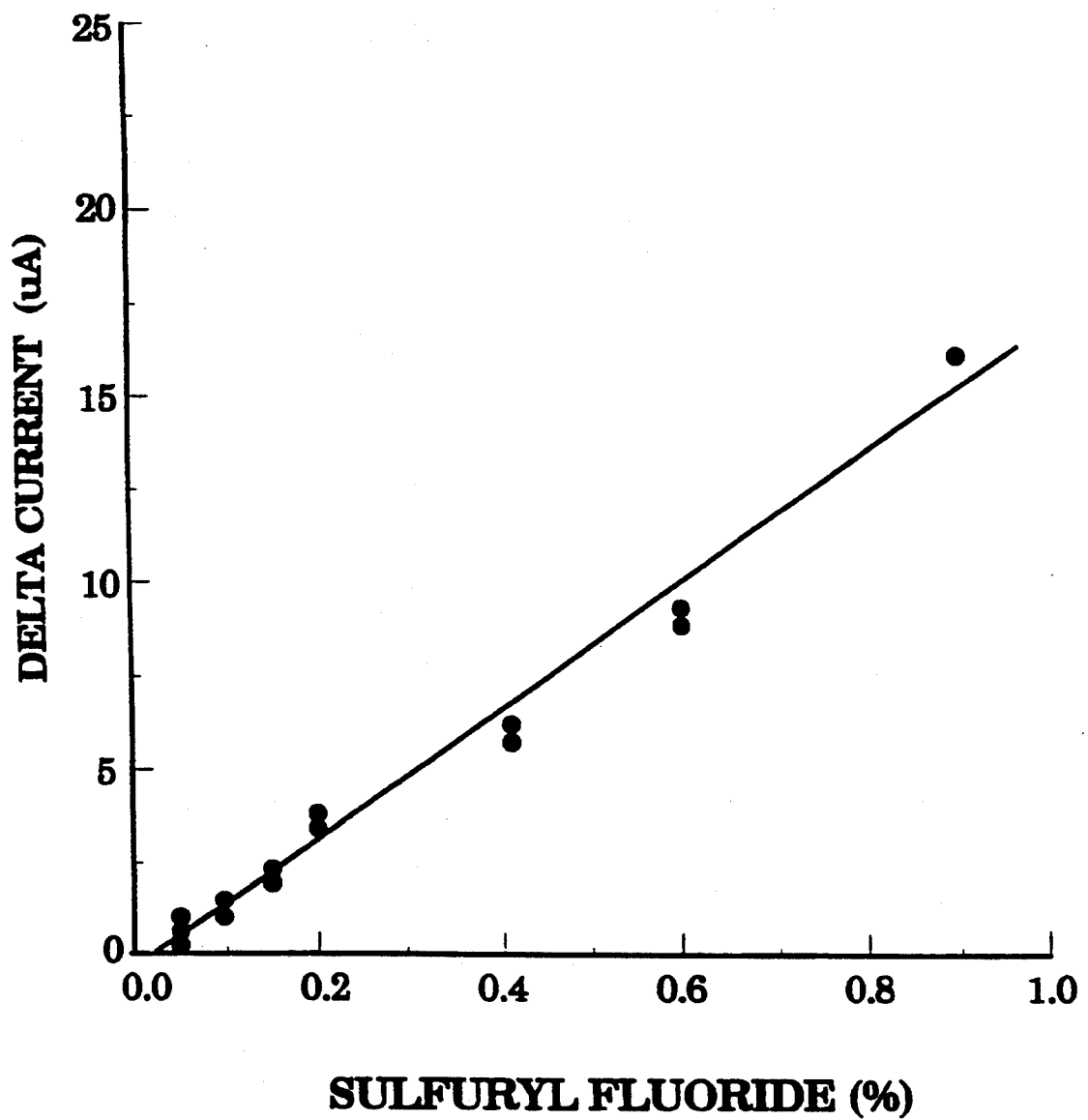
FIG. 14 is a calibration curve for one embodiment of the invention as used in an amperometric mode to detect sulfuryl fluoride.

This Example used a three-electrode, two-film arrangement. A gold working electrode was used with a platinum mesh reference electrode and a platinum counter electrode, and the films were each comprised of tetrabutylammonium trifluoromethanesulfonate at 13.3 weight percent, poly(ethylene glycol) tetrahydrofurfuryl ether (as the complexing agent) at 46.7 weight percent, 9.3 weight percent of epoxidized soybean oil and the remainder of poly(vinyl chloride). The bias potential was a negative 1.0 volts as applied by a commercially-available potentiostat to give a baseline cathodic current of about 8 microamperes. When contacted with various concentrations of sulfuryl fluoride in air in the flow cell arrangement described in Example 1 and used in each of the previous examples, additional current resulted and was measured as indicated in the data of Table 5 and in the corresponding calibration curve of FIG. 14.

TABLE 5

| Pct. $SO_2F_2$ | Change in Current (uA) |
|---|---|
| 0.05 | 0.94 |
| 0.05 | 1.36 |
| 0.05 | 0.80 |
| 0.10 | 1.60 |
| 0.10 | 1.45 |
| 0.15 | 2.10 |
| 0.15 | 2.15 |
| 0.20 | 3.15 |
| 0.20 | 3.45 |
| 0.41 | 6.05 |
| 0.41 | 6.35 |
| 0.61 | 9.15 |
| 0.61 | 9.25 |
| 0.90 | 16.40 |

EXAMPLE 6

Figure 15:
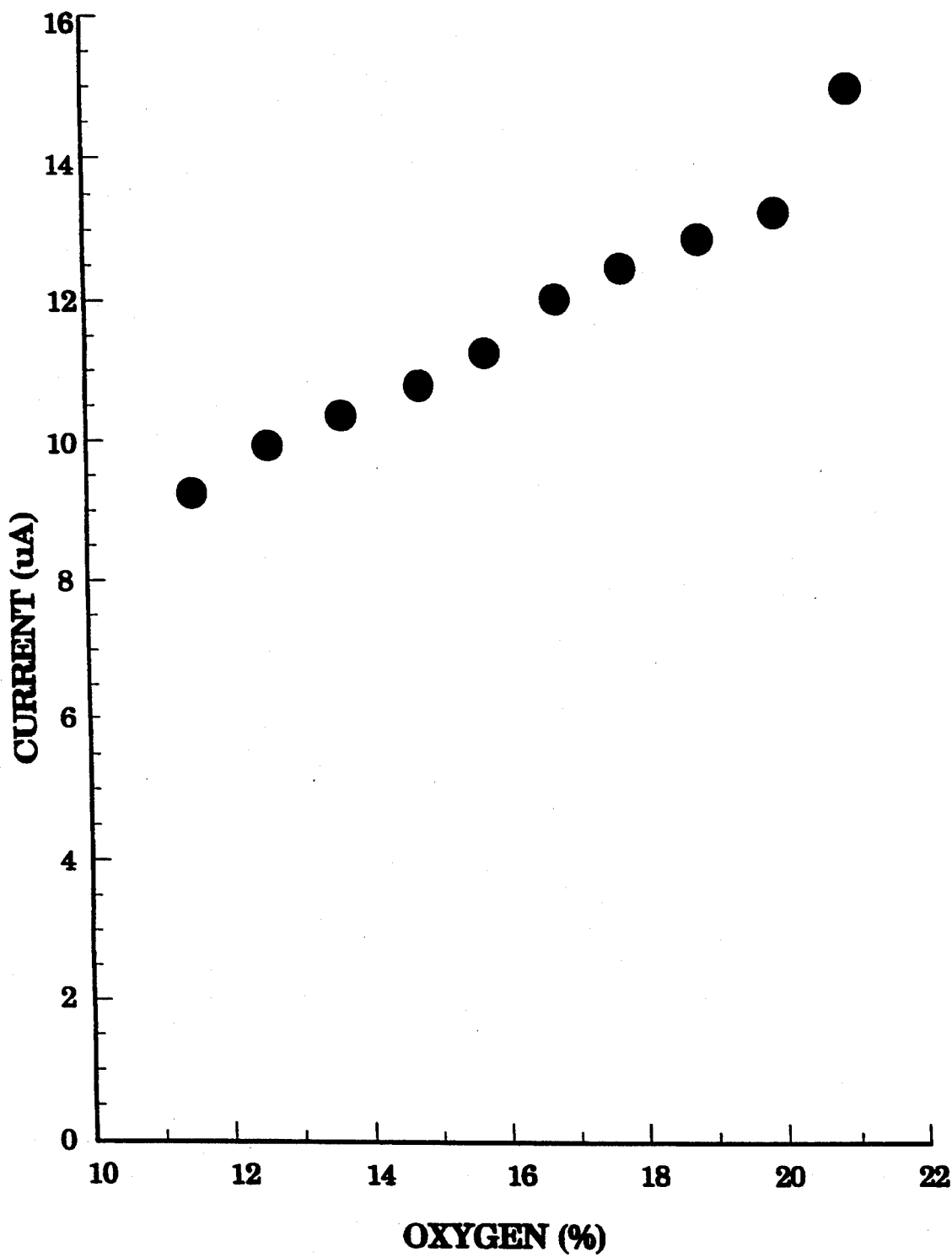
FIG. 15 is a calibration curve for an embodiment of the invention as used in an amperometric mode to detect oxygen in a given environment.

The electrode array of FIG. 6 was used for this Example, with the electrolyte salt of the film being lithium chloride at 18.2 percent by weight, the inert polymer being poly(vinylidene fluoride) at 54.5 weight percent, and the complexing agent being the TegMeR ™ 804 tetraethylene glycol di-(2-ethylhexanoate) material. The bias potential was a negative 1.5 volts versus platinum, as applied by a commercially-available potentiostat. A baseline cathodic current was established in this set-up at 15 microamperes in air (21 percent oxygen). Upon addition of nitrogen to this air environment, reduced concentrations of oxygen were indicated as reductions in the measured current, as shown in Table 6 and in the calibration curve of FIG. 15.

TABLE 6

| Pct. $O_2$ | Cathodic Current (uA) |
| --- | --- |
| 19.95 | 13.26 |
| 18.9 | 12.91 |
| 17.85 | 12.50 |
| 16.8 | 12.12 |
| 15.75 | 11.38 |
| 14.7 | 10.80 |
| 13.65 | 10.41 |
| 12.6 | 9.91 |
| 11.55 | 9.25 |
| 10.5 | 8.40 |

EXAMPLE 7

Figure 16:
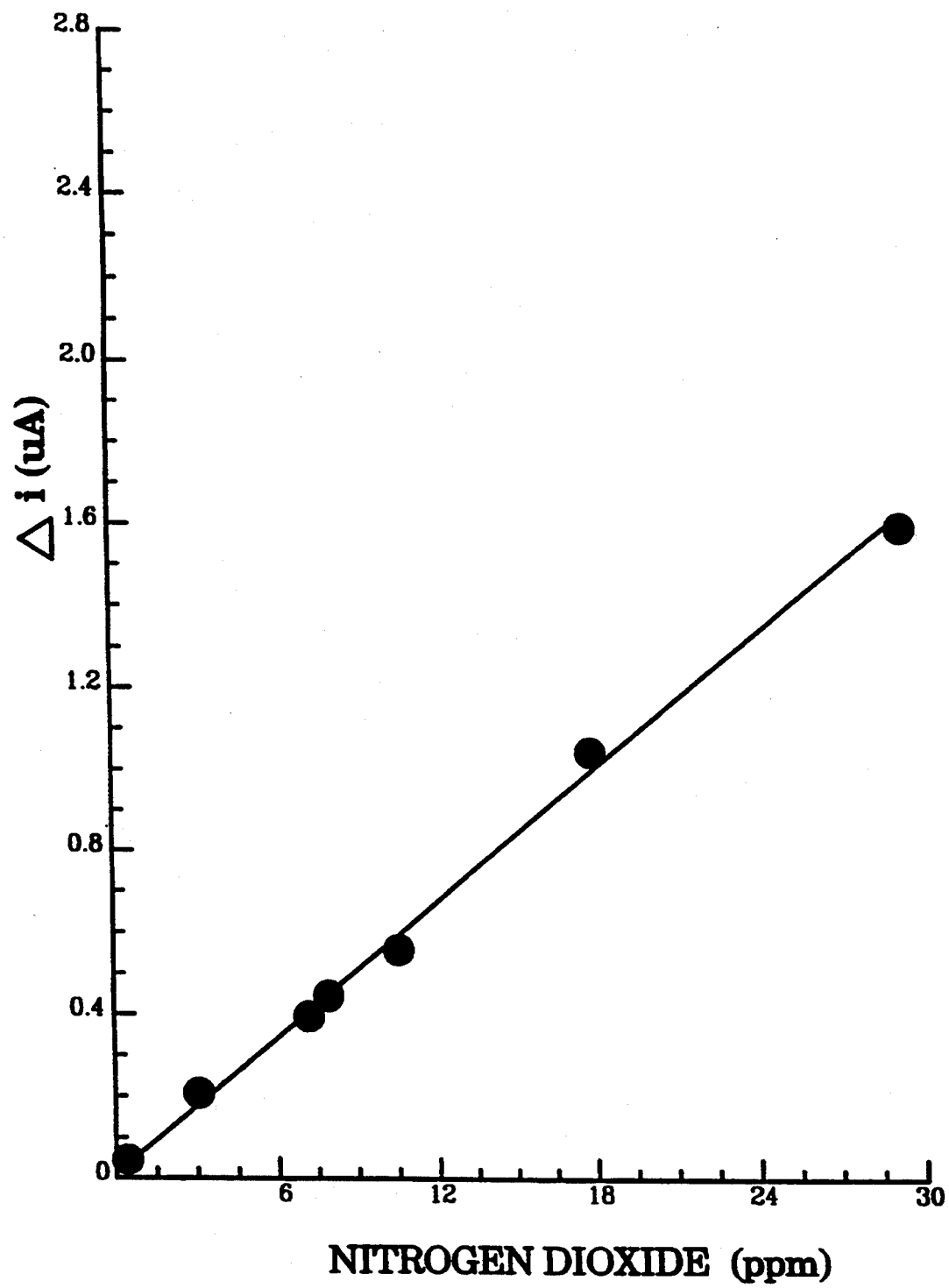
FIG. 16 is a calibration curve for one embodiment of the invention as used in an amperometric mode to detect nitrogen dioxide.

This Example used again a three-electrode, two film apparatus with platinum working, counter and reference electrodes. The films were comprised of 46 weight percent of poly(vinyl chloride), 23 weight percent of the TegMeR ™ 804 material, 23 weight percent of lithium nitrate as the electrolyte salt, and 8 weight percent of epoxidized soybean oil. The bias potential applied was positive 1.0 volts, and a baseline anodic current of about 1 microamperes was established. When contacted with various concentrations of nitrogen dioxide in air via the apparatus employed in earlier examples, additional current was correspondingly produced to provide the data shown in Table 7 and the corresponding calibration curve of FIG. 16.

TABLE 7

| PPM of $NO_2$ | Change in Current (uA) |
| --- | --- |
| 0.8 | 0.05 |
| 3.0 | 0.20 |
| 7.5 | 0.36 |
| 8.4 | 0.43 |
| 10.5 | 0.53 |
| 18.0 | 1.03 |
| 29.3 | 1.55 |

EXAMPLE 8

Figure 17:
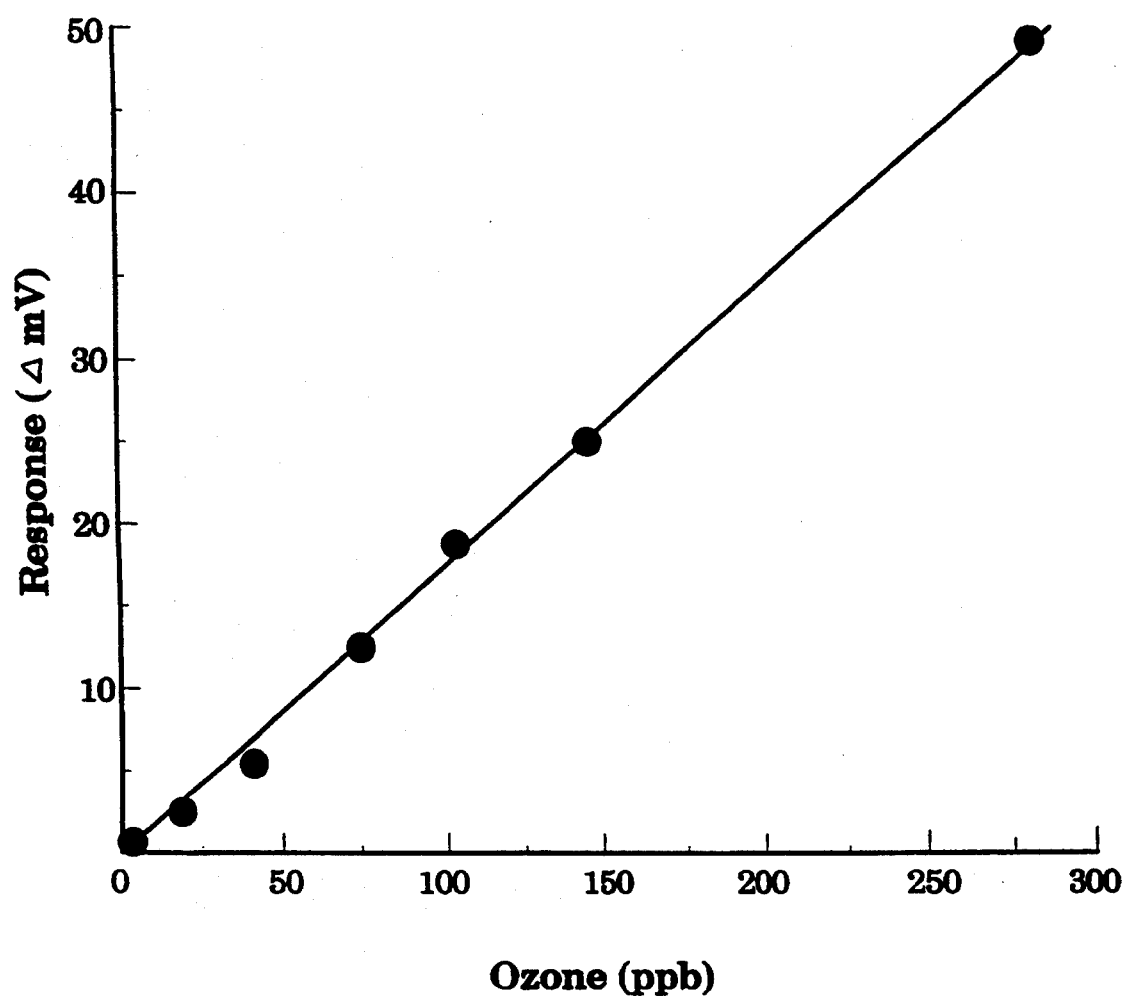
FIG. 17 is a calibration curve for one embodiment of the invention as used in a galvanic mode to detect ozone.

The galvanic apparatus of Example 2 was used in this Example to detect ozone. Various concentrations of ozone in air were brought into contact with the sensor and voltage measurements, as further amplified by a commercially-available device for this purpose, were taken at these various part per billion (ppb) concentrations. The results obtained are as shown in Table 8, and the calibration curve obtained is shown in FIG. 17.

TABLE 8

| PPM of Ozone | Change in Voltage (mV) |
| --- | --- |
| 0 | 0 |
| 18 | 2 |
| 38 | 4 |

TABLE 8-continued

| PPM of Ozone | Change in Voltage (mV) |
| --- | --- |
| 76 | 12 |
| 105 | 18 |
| 152 | 24 |
| 288 | 48 |

EXAMPLE 9

Figure 18:
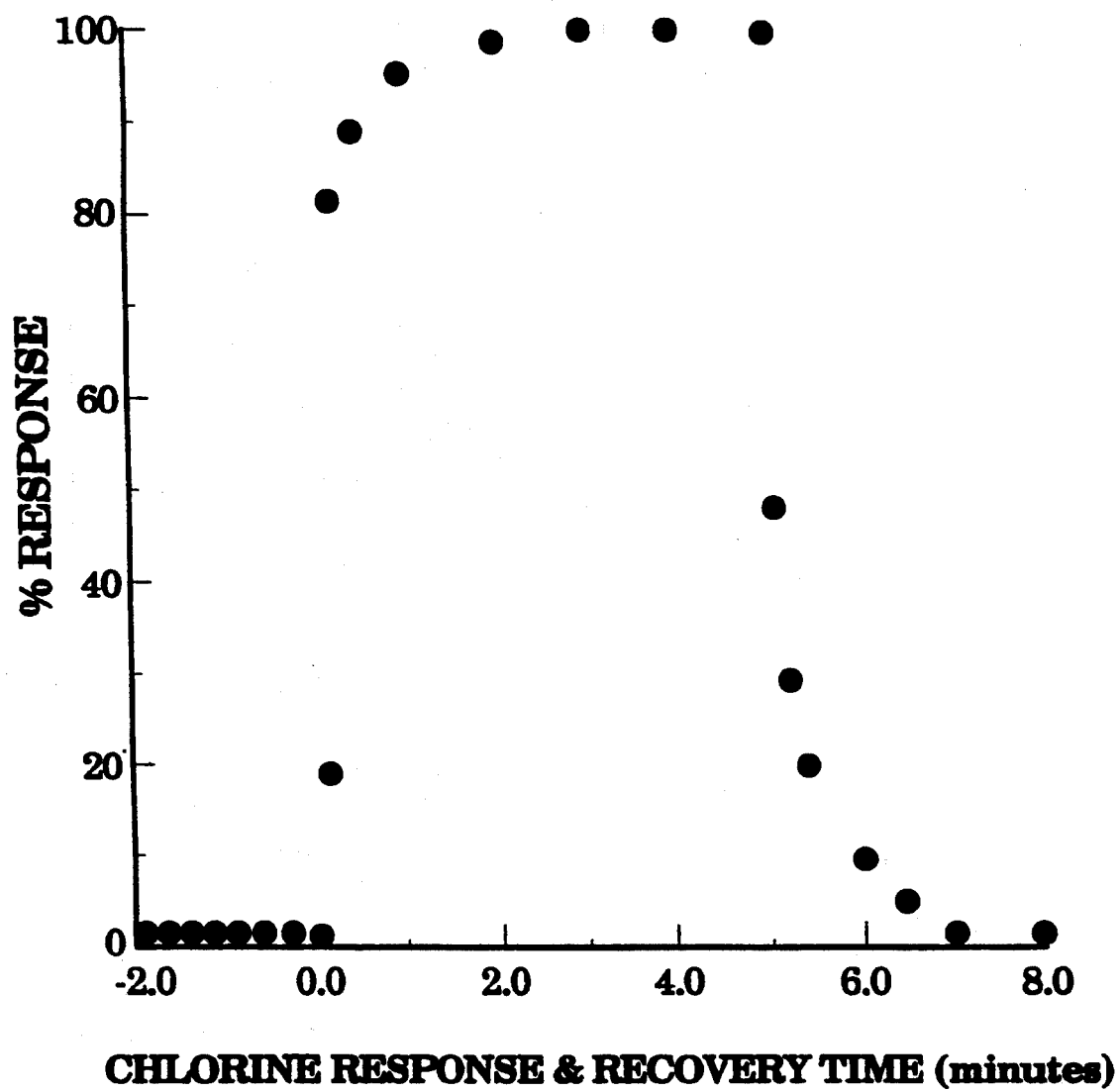
FIG. 18 are typical response and recovery data for the detection of chlorine via a preferred embodiment operating in an amperometric mode.

In this example, an apparatus was constructed with platinum working and counter electrodes and a silver/silver chloride reference electrode arrayed as illustrated in FIG. 6. A single 0.5 inch diameter film was prepared for use in the apparatus which comprised 1.0 grams of poly(vinyl chloride), 4.0 grams of the TegMeR ™ 804 material as a complexing agent, 0.1 grams of epoxidized soybean oil and 0.57 grams of tetrabutylammonium chloride as an electrolyte material. The apparatus was exposed to a concentration of 6.5 parts per million (ppm) of chlorine in air and the response of the apparatus measured as a function of time. When it appeared that an equilibrium value had been reached, the chlorine flow was stopped and the recovery of the sensor tracked over time. The collected measurements are provided in Table 9, and illustrated in part in FIG. 18 (the last two measurements are not plotted).

TABLE 9

| Time (Min.) | Pct. of Equilibrium Response |
| --- | --- |
| 0 | 0 |
| 0.17 | 18 |
| 0.33 | 82 |
| 0.50 | 88 |
| 0.67 | 91 |
| 0.83 | 93 |
| 1.00 | 95 |
| 1.50 | 97 |
| 2.00 | 98 |
| 3.00 | 100 |
| 4.00 | 100 |
| 5.00 | 100 |
| 5.17 | 47 |
| 5.33 | 29 |
| 5.50 | 20 |
| 5.67 | 15 |
| 5.83 | 11 |
| 6.00 | 10 |
| 6.50 | 6 |
| 7.00 | 5 |
| 8.00 | 2 |
| 9.00 | 1 |
| 10.00 | 0 |

EXAMPLE 10

This example utilized a two electrode, interdigitated microsensor electrode array (IME) as depicted in FIG. 19. The platinum working and counter electrodes 24 and 26 were fabricated into the illustrated IME by Silica Source Technology Corp., Tempe, Ariz. The interdigit or interelectrode gap was 12 micrometers and the electrode width was 20 micrometers. Each digit was 0.5 mm long, and there were 12 digits per electrode 24 or 26. Lead wires were connected to the platinum contact pads for electrodes 24 and 26 with silver paint, and isolated from the environment with epoxy.

A drop of a solution of 3 grams of poly(vinylidene fluoride), 1.2 grams of the TegMeR ™ 804 material and 0.6 grams of lithium chloride in dimethylformamide was then applied to the IME, and the DMF solvent evaporated off. A bias potential of a negative 0.2 volts was then applied via a commercially-available Model 273A potentiostat from Princeton Applied Research, in a two electrode amperometric mode of operation. Upon establishing a baseline cathodic current (at about 1.5 nanoamps), the sensor apparatus was exposed to a concentration of 250 parts per million of chlorine in air and the response of the apparatus tracked as a function of time from the application of the bias potential. Upon reaching an equilibrium value, the chlorine flow was stopped, and the recovery of the sensor tracked as well. The results are shown in Table 10 as follows:

TABLE 10

| Time (Secs) | Current (Amps $\times 10^{-9}$) |
|---|---|
| 133 | 3.8 |
| 215 | 1.9 |
| 296 | 1.5 |
| 313 | 21.8 |
| 326 | 49.4 |
| 343 | 77.1 |
| 379 | 108.8 |
| 431 | 124.1 |
| 482 | 130.4 |
| 549 | 134.5 |
| 596 | 135.9 |
| 618 | 108.7 |
| 634 | 76.8 |
| 651 | 51.9 |
| 697 | 19.9 |
| 751 | 8.3 |
| 806 | 4 |
| 873 | 1.9 |

EXAMPLE 11

The same IME was employed here as in Example 10, but the film was prepared from a solution of 65 percent by weight of poly(vinyl chloride), 6 weight percent of epoxidized soybean oil and 29 weight percent of the TegMeR TM 804 complexing agent in tetrahydrofuran. A drop of this solution was placed on the IME, and the THF evaporated off to leave a 0.01 cm.-thick film.

A bias potential of 2.5 volts was applied using the setup of Example 10, and on establishing a baseline anodic current in air, the sensor apparatus was (at just over about 5000 seconds in the Table below) exposed to a concentration of 300 parts per million of HCl in air. The response of the apparatus was tracked again as a function of time, as well as its recovery on a cessation of the HCl flow through the flow cell after about 9200 seconds. The results are shown in Table 11:

TABLE 11

| Time (Secs) | Anodic Current (Amps $\times 10^{-9}$) |
|---|---|
| 0 | 2.8 |
| 4760 | 2.5 |
| 5196 | 7.1 |
| 5270 | 9.7 |
| 5271 | 13.5 |
| 6036 | 15.8 |
| 7613 | 16.8 |
| 9189 | 16.7 |
| 9459 | 10.7 |
| 9460 | 8.8 |
| 9729 | 6.9 |
| 10495 | 5.3 |
| 11576 | 4.0 |
| 15225 | 3.0 |
| 20000 | 2.4 |

EXAMPLE 12

For this Example, a three-electrode IME as shown in FIG. 21 was employed from AAI-ABTECH, Yardley, Pa., using platinum working, counter and reference electrodes. This IME was spray-coated with a solution containing 1 gram of poly(vinylidene fluoride), 0.75 grams of the TegMeR TM 804 tetraethylene glycol di-(2-ethylhexanoate) complexing agent, and 0.2 grams of lithium chloride in 50 mL of dimethylformamide. After evaporating off the DMF, the coated IME was connected to a voltmeter through a 15 megaohm resistor, and exposed (at 18.3 percent relative humidity and an ambient temperature of 18.8 degrees Celsius, an applied bias potential of 0.060 volts and without a protective film) to 4.2 parts per million of chlorine in air. The response of the sensor in microamps (cathodic current) was tracked as a function of time, and when an equilibrium value appeared to have been reached, the chlorine flow was shut off and the recovery of the sensor also tracked over time. The measurements taken are shown in Table 12:

TABLE 12

| Time (Secs) | Current (Microamps) |
|---|---|
| 0 | 0 |
| 10 | 0.066 |
| 20 | 0.129 |
| 30 | 0.157 |
| 40 | 0.168 |
| 50 | 0.176 |
| 60 | 0.18 |
| 90 | 0.183 |
| 120 | 0.185 |
| 240 | 0.186 |
| 250 | 0.156 |
| 260 | 0.084 |
| 270 | 0.052 |
| 280 | 0.039 |
| 290 | 0.032 |
| 300 | 0.027 |
| 330 | 0.022 |
| 360 | 0.018 |
| 480 | 0.013 |
| 540 | 0.012 |
| 720 | 0.011 |

What is claimed is:

1. A sensor apparatus for detecting a compound of interest or for determining changes in the concentration of such compound from a baseline concentration, said apparatus including in an electrical circuit:
   a non-plasticized polymer film which acts in an electrolytic capacity and which is comprised of a substantially inert, noncomplexing polymeric matrix, a complexing agent and an electrolyte material dissociatingly soluble in the complexing agent, wherein each of these materials is compatible with one another and with ionic species generated from the compound of interest;
   electrodes in electrical contact with the polymer film; and
   measuring apparatus associated with said electrodes for measuring a change in voltage or current in the circuit responsive to the presence of the compound in an environment surrounding the polymer film or responsive to a change in the concentration of such compound in such environment from a baseline: concentration.

2. A sensor apparatus for detecting a compound of interest or for determining changes in the concentration of such compound from a baseline concentration, said apparatus including in an electrical circuit:

a polymer film which acts in an electrolytic capacity and which does not contain an electrolyte material for imparting conductivity to the film but which is otherwise comprised of a substantially inert, non-complexing polymeric matrix, and a complexing agent which is compatible with ionic species generated from said compound and which is either of a plasticizing or non-plasticizing nature with respect to the noncomplexing polymeric matrix;

electrodes in electrical contact with the polymer film; and measuring apparatus associated with said electrodes for measuring a change in voltage or current in the circuit responsive to the presence of the compound in an environment surrounding the polymer film or responsive to a change in the concentration of such compound in such environment from a baseline concentration.

3. A sensor apparatus for detecting an ionizable compound of interest or for determining changes in the concentration of such compound from a baseline concentration through the dissociation of such ionizable compound into ionic species, said apparatus including in an electrical circuit:

a polymer film which acts in an electrolytic capacity and which is comprised of a substantially inert, noncomplexing polymeric matrix and a complexing agent which dissociates the ionizable compound and is compatible with the resulting ionic species;

working and counter electrodes in electrical contact with the polymer film;

a power source for applying a voltage between the working and counter electrodes; and measuring apparatus electrically connected to the electrodes and which indicates a change in voltage or current flow between the electrodes and across or through the film responsive to an ionizable compound contacting the polymer film and being dissociated therein into ionic species or responsive to a change in the number of molecules of such ionizable compound contacting the polymer film over a period of time from a baseline number.

4. The apparatus of claim 3, wherein the working and counter electrodes are positioned against opposite faces of the polymer film.

5. The apparatus of claim 4, wherein the working and counter electrodes and intervening polymer film are compressed together as an assembly through the use of a resilient compression member pressing directly or indirectly against said assembly.

6. The apparatus of claim 5, further comprising a barrier film positioned between a fluid environment to be monitored and the working electrode which is selectively permeable to the compound of interest but which substantially prevents or restricts potentially interfering compounds in the fluid environment from contacting said working electrode, and wherein the working and counter electrodes, the intervening polymer film and the barrier film are compressed together as an assembly through the use of a resilient compression member pressing directly or indirectly against said assembly.

7. The apparatus of claim 5, further comprising a protective film which prevents dirt, other particulate matter and rain from encountering the working electrode, and wherein the working and counter electrodes, the intervening polymer film and the protective film are compressed together as an assembly through the use of a resilient compression member pressing directly or indirectly against said assembly.

8. The apparatus of claim 3, wherein the working and counter electrodes are in a coplanar arrangement on an electrically insulative supporting surface which contacts the polymer film.

9. The apparatus of claim 8, wherein the working and counter electrodes are arranged as strips on said electrically insulative supportive surface.

10. The apparatus of claim 8, wherein the working and counter electrodes are in the form of a flat ring and disk adhered in place by an electrically insulative medium.

11. The apparatus of claim 8, wherein the working and counter electrodes are in the form of an interdigitated microelectrode array fabricated on said electrically insulative supportive surface.

12. The apparatus of any one of claims 4, 8, 9, 10 or 11, further comprising a barrier film positioned between a fluid environment to be monitored and the working electrode or the polymer film and which is selectively permeable to the compound of interest but substantially prevents or restricts potentially interfering compounds in the fluid environment from contacting said working electrode or said polymer film.

13. The apparatus of claim 12, further comprising a protective film which prevents dirt, other particulate matter and rain from encountering the film or an electrode of said apparatus.

14. The apparatus of any one of claims 4, 8, 9, 10 or 11, further comprising a protective film which prevents dirt, other particulate matter and rain from encountering the film or an electrode of said apparatus.

15. A sensor apparatus for detecting a compound of interest or for determining changes in the concentration of such compound from a baseline concentration through the oxidation or reduction of such compound into ionic species, said apparatus including in an electrical circuit:

a non-plasticized polymer film which acts in an electrolytic capacity and which is comprised of a substantially inert polymeric matrix, a complexing agent and an electrolyte material dissociatingly soluble in the complexing agent, wherein each of these materials is compatible with one another and with ionic species generated from the oxidation or reduction of the compound of interest;

working and counter electrodes in electrical contact with the polymer film and which are composed of materials which are dissimilar to provide a net spontaneous reaction; and measuring apparatus associated with said working and counter electrodes for indicating a change in voltage or current flow between the electrodes and across or through the film responsive to tile oxidation or reduction of the compound to the ionic species at the working electrode, or responsive to a change in the number of molecules oxidized or reduced of such compound at the working electrode over a period of time from a baseline number.

16. A sensor apparatus for detecting a compound of interest or for determining changes in the concentration of such compound from a baseline concentration through the reduction or oxidation of such compound into ionic species, said apparatus including in an electrical circuit:

a non-plasticized polymer film which acts in an electrolytic capacity and which is comprised of a substantially inert polymeric matrix, a complexing agent and an electrolyte material dissociatingly soluble in the complexing agent, wherein each of these materials is compatible with one another and with ionic species generated from the oxidation or reduction of the compound of interest;

a two-electrode combination of a working electrode and a counter electrode, or a three-electrode combination of a working electrode, a counter electrode and a reference electrode, all in electrical contact with the polymer film;

a power source for applying a voltage between the working and counter electrodes in the two-electrode combination or between the working and reference electrodes in the three-electrode combination; and measuring apparatus associated with said electrodes for indicating a change in voltage or current flow between the electrodes and across or through the film responsive to the oxidation or reduction of the compound at the working electrode into ionic species or responsive to a change in the number of molecules of such compound oxidized or reduced at the working electrode over a period of time from a baseline number.

17. A process for detecting a compound of interest or for determining changes in the concentration of such compound from a baseline concentration within an industrial process stream or within an aggregation of flowable materials in a process conduit or vessel wherein such compound is found, comprising:

placing a sensor apparatus in operative contact with the stream or aggregation of flowable materials which includes in an electrical circuit a polymer film which acts in an electrolytic capacity and which comprises a substantially inert, noncomplexing polymeric matrix and a complexing agent which is compatible with ionic species generated from the compound;

electrodes in electrical contact with the polymer film; and measuring apparatus associated with said electrodes for measuring a change in voltage or current in the circuit responsive to the presence of the compound in the stream or aggregation or responsive to a change in the concentration of such compound in such stream or aggregation from a baseline concentration; and monitoring the voltage or current in the circuit via said measuring apparatus.

18. A process as defined in claim 17, wherein the industrial process stream is the product stream from a reactive chemical manufacturing process.

19. A process as defined in claim 17, wherein the industrial process stream is the effluent stream from a vent stack.

* * * * *